United States Patent [19]
Bundy et al.

[11] 4,029,693
[45] June 14, 1977

[54] 2a,2b-DIHOMO-11-DEOXY-17(SUBSTITUTED PHENYL)-18,19,20-TRINOR-PGE$_2$ COMPOUNDS AND THEIR CORRESPONDING ESTERS

[75] Inventors: Gordon L. Bundy, Kalamazoo; Norman A. Nelson, Galesburg, both of Mich.

[73] Assignee: The Upjohn Company, Kalamazoo, Mich.

[22] Filed: Jan. 20, 1975

[21] Appl. No.: 542,372

[52] U.S. Cl. .................... 260/473 R; 260/343.3 R; 260/346.2 R; 260/520 R
[51] Int. Cl.$^2$ ................. C07C 63/33; C07C 69/76; A61K 31/19; A61K 31/25; C07C 177/00
[58] Field of Search .................... 260/473 R, 520 R

[56] References Cited
FOREIGN PATENTS OR APPLICATIONS 7,301,094   7/1973   Netherlands ..................... 260/520

OTHER PUBLICATIONS

"Medicinal Chem" Burger, 3rd Edition, Part I, pp. 64–72 (1970).
Takeda Chemical Ind. Ltd., Derwent Pub., Pub. 2/27/73, Published Japanese App.
Roussel UCIAF, French Pat. 2206091, Derwent Pub. 11/16/72.

Primary Examiner—Norman Morgenstern
Attorney, Agent, or Firm—Robert A. Armitage

[57] ABSTRACT

This invention comprises 11-deoxy-17-phenyl-18,19,20-trinor-prostaglandin-type compounds which exhibit prostaglandin-type pharmacological activity, such as lowering blood pressure, inhibiting gastric secretion, regulating the reproductive cycle, and the like.

22 Claims, No Drawings

2a,2b-DIHOMO-11-DEOXY-17(SUBSTITUTED PHENYL)-18,19,20-TRINOR-PGE$_2$ COMPOUNDS AND THEIR CORRESPONDING ESTERS

BACKGROUND OF THE INVENTION

This invention relates to novel compositions of matter, to novel methods for producing those, to novel chemical intermediates useful in those processes. Particularly, this invention relates to certain novel analogs of some of the known prostaglandins which differ from the known PGE and PGF compounds in that the 11-hydroxy is replaced by hydrogen and the methyl terminated side chain is shortened by 3 carbon atoms and substituted at C-17 by an aromatic ring. The known prostaglandins (PG's) include, for example, prostaglandin (PGE$_1$), prostaglandin E$_2$ (PGE$_2$), dihydroprostaglandin E$_1$ (dihydro-PGE$_1$), prostaglandin F$_{1\alpha}$ (PGF$_{1\alpha}$), prostaglandin F$_{2\alpha}$ (PGF$_{2\alpha}$), dihydroprostaglandin F$_{1\alpha}$ (dihydro-PGF$_{1\alpha}$), prostaglandin F$_{1\beta}$ (PGF$_{1\beta}$), prostaglandin F$_{2\beta}$ (PGF$_{2\beta}$), dihydroprostaglandin F$_{1\beta}$ (dihydro-PGF$_{1\beta}$). Each of the above-mentioned known prostaglandins is a derivative of prostanoic acid which has the following structure and carbon atom numbering

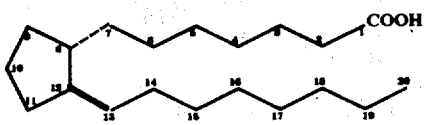

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

PGE$_1$ has the following structure:

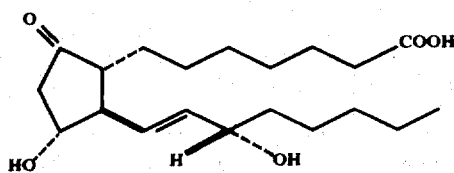

PGE$_2$ has the following structure:

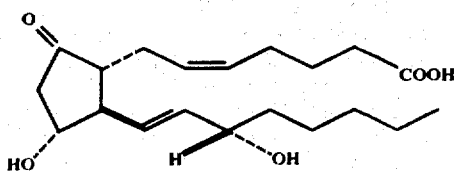

Dihydro-PGE$_1$ has the following structure:

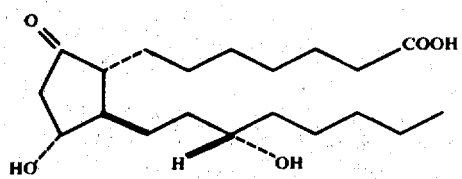

PGF$_{1\alpha}$ has the following structure:

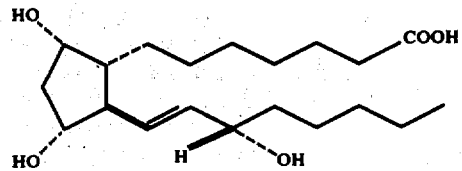

PGF$_{2\alpha}$ has the following structure:

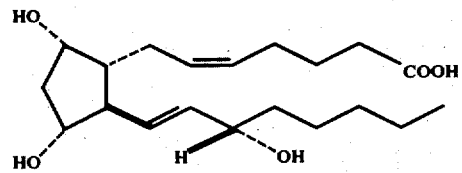

Dihydro-PGF$_{1\alpha}$ has the following structure:

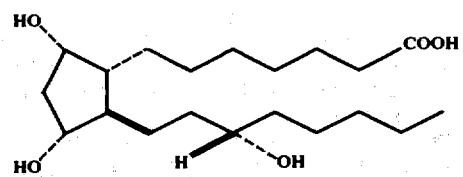

PGF$_{1\beta}$ has the following structure:

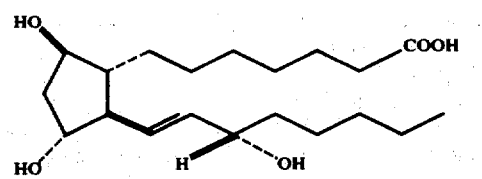

PGF$_{2\beta}$ has the following structure:

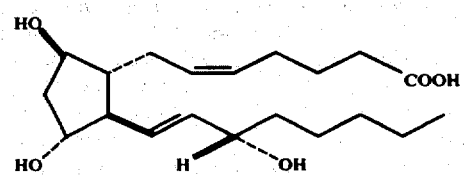

Dihydro-PGF$_{1\beta}$ has the following structure:

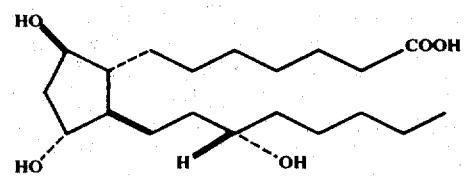

In the above formulas, as well as in the formulas hereinafter given, broken line attachments to the cyclopentane ring indicate substituents in alpha configuration i.e., below the plane of the cyclopentane ring. Heavy solid line attachments to the cyclopentane ring indicate substituents in beta configuration, i.e., above the plane of the cyclopentane ring.

Wavy line (~) attachments herein indicate substituents in the alpha position, the beta position, or in a mixture of alpha and beta positions.

The side-chain hydroxy at C-15 in the above formulas is in S configuration. See, Nature 212, 38 (1966) for discussion of the stereochemistry of the prostaglandins. Expressions such as C-15, and the like, refer to the carbon atom in the prostaglandin or prostaglandin analog which is in the position corresponding to the position of the same number in prostanoic acid.

Molecules of the known prostaglandins each have several centers of asymmetry, and can exist in racemic (optically inactive) form and in either of the two enantiomeric (optically active) forms i.e. the dextrorotatory and levorotatory forms. As drawn, the above formulas each represent the particular optically active form of the prostaglandin which is obtained from certain mammalian tissues, for example, sheep vesicular glands, swine lung, or human seminal plasma, or by carbonyl and/or double bond reduction of that prostaglandin. See, for example, Bergstrom et al., cited above. The mirror image of each of these formulas represents the other enantiomer of that prostaglandin. The racemic form of a prostaglandin contains equal numbers of both enantiomeric molecules, and one of the above formulas and the mirror image of that formula is needed to represent correctly the corresponding racemic prostaglandin. For convenience hereinafter, use of the terms, $PGE_1$, $PGE_2$, $PGF_{1\alpha}$, $PGF_{2\alpha}$, $PGF_{1\beta}$, $PGF_{2\beta}$ and the like, refer to the optically active form of that prostaglandin with the same absolute configuration as $PGE_1$ obtained from mammalian tissues. When reference to the racemic form of one of those prostaglandins is intended, the word "racemic" or "dl" will precede the prostaglandin name.

$PGE_1$, $PGE_2$, $PGF_{1\alpha}$, $PGF_{2\alpha}$, $PGF_{1\beta}$, and $PGF_{2\beta}$ and their esters, acylates and pharmacologically acceptable salts, are extremely potent in causing various biological responses. For that reason, these compounds are useful for pharmacological purposes. See, for example, Bergstrom et al., Pharmacol. Rev. 20, 1 (1968) and references cited therein. A few of those biological responses are systemic blood pressure lowering in the case of the PGE and $PGF_\beta$ compounds as measured, for example, in anesthetized (pentobarbital sodium) pentolinium-treated rats with indwelling aortic and right heart cannulas; stimulation of smooth muscle as shown, for example, by tests on strips of guinea pig ileum, rabbit duodenum, or gerbil colon; potentiation of other smooth muscle stimulants; lipolytic activity as shown by antagonism of epinephrine-induced mobilization of free fatty acids or inhibition of the spontaneous release of glycerol from isolated rat fat pads; inhibition of gastric secretion in the case of the PGE compounds as shown in dogs with secretion stimulated by food or histamine infusion; activity on the central nervous system; controlling spasm and facilitating breathing in asthmatic conditions; and decreasing blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits and monkeys.

For example, these compounds and especially the PGE compounds, are useful in mammals, including man, as nasal decongestants. For this purpose, the compounds are used in a dose range of about 10 $\mu$g. to about 10 mg. per ml. of a pharmacologically suitable liquid vehicle or as an aersol spray, both for topical application.

The PGE and $PGF_\beta$ compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other antiasthmatic agents, such as sympathomimetics (isoproterenol, phenylephrine, epinephrine, etc.); xanthine derivatives (theophylline and aminophylline); and corticosteroids (ACTH and predinisolone). Regarding use of these compounds see M. E. Rosenthale, et al., U.S. Pat. No. 3,644,638.

The PGE compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 $\mu$g. to about 500 $\mu$g. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, $PGF\alpha$ and $PGF_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent postoperativethrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, PGF$\alpha$, and PGF$\beta$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, PGE compound, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE and PGF$\beta$ compounds are useful as hypotensive agents to reduce blood pressure in mammals, including man. For this purpose, the compounds are administered by intravenous infusion at the rate about 0.01 to about 50 $\mu$g. per kg. of body weight per minute or in single or multiple doses of about 25 to 500 $\mu$g. per kg. of body weight total per day.

The PGE, PGF$\alpha$, and PGF$\beta$ compounds are useful in place of oxytocin to reduce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, PGF$\alpha$, and PGF$\beta$ compounds are useful for controlling the reproductive cycle in menstrating female mammals. By the term menstrating female mammals is meant animals which are mature enough to menstrate but not so old that regular menstration has ceased. For that purpose the prostaglandin is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first and second trimester of the normal mammalian gestation period.

The PGE and PGF compounds are useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by PGE and PGF compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the PGE and PGF compounds are administered locally or systemically.

PGE$_2$, for example, is administered orally or vaginally at doses of about 5 to 50 mg. per treatment of an adult female human, with from one to five treatments per 24 hour period. PGE$_2$ is also administered intramuscularly or subcutaneously at doses of about one to 25 mg. per treatment. The exact dosages for these purposes depend on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGE, PGF$\alpha$, and PGF$\beta$ compounds are also useful in reducing the undesirable gastrointestinal effects resulting from systemic administration of anti-inflammatory prostaglandin synthetase inhibitors, and are used for that purpose by concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including PGE$_1$, PGE$_2$, PGE$_3$, 13,14-dihydro-PGE$_1$, and the corresponding 11-deoxy-PGE compounds. The prostaglandins are useful, for example, in reucing the undesirable gastrointestinal effects resulting from systemic administration of indomethacin, phenylbutazone, and aspirin. These are substances specifically mentioned in Partridge et al. as non-steroidal anti-inflammatory agents. But these are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally, or, alternatively, orally or, in the case of women vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

The PGF$_\alpha$ compounds are useful in the treatment of shock (hemorrhagic shock, endotoxin shock, cardiogenic shock, surgical shock, or toxic shock). Shock is marked by pallor and claminess of the skin, decreased blood pressure, feeble and rapid pulse, decreased respiration, restlessness, anxiety, and sometimes unconsciousness. Shock usually follows cases of injury and trauma. Expert and fast emergency measures are required to successfully manage such shock conditions. Accordingly, prostaglandins, combined with a pharmaceutical carrier which adapts the prostaglandin for intramuscular, intravenous, or subcutaneous use, are useful, especially in the early stages of shock where increased blood pressure is a critical factor, for aiding and maintaining adequate blood flow, perfusing the vital organs, and exerting a presser response by constricting veins and raising blood pressure to normal levels. Accordingly, the prostaglandins are useful in preventing irreversable shock which is characterized by a profound fall in blood pressure, dilation of veins, and venus blood pooling. In the treatment of shock, the prostaglandin is infused at a dose of 0.1 – 25 mcg./kg./min. The prostaglandin may advantageously be combined with known vasoconstrictors; such as phenoxybenzamine, norepinephrine, norephrine, and the like. Further, when used in the treatment of shock the prostaglandin may be combined with steroids (such as, hydrocortisone or methylprednisolone), tranquilizers, and antibiotics (such as lincomycin or clindamycin).

The PGE, PGF$_\alpha$, and PGF$_\beta$ are useful in domestic animals as an abortifacient (especially for feedlot heifers), as an aid to estrus detection, and for regulation or synchronization of estrus. Domestic animals include horses, cattle, sheep and swine.

The regulation or synchronization of estrus, as well as estrus detection, allows for more efficient management of both conception and labor by enabling a herdsman to breed all his female animals in short predefined intervals. This results in a higher percentage of live births than the percentage achieved by natural control. The prostaglandin is injected or applied in a feed at doses of 0.1–100 mg. per animal per day and may be combined with other agents such as steroids. Dosing schedules will depend on the species treated. For example, mares are given prostaglandin 5–8 days after ovulation and return to estrus. Cattle, are treated at regular intervals over a 3 week period to advantageously bring all into estrus at the same time.

11-deoxy-17-phenyl prostaglandin-type compounds are known in the art. For example, Netherlands Patent No. 7,301,094 (Derwent Farmdoc 46023U) issued to Wisconsin Alumni Research Foundation claims 11-deoxy-17-phenyl-18,29,20-trinor-PGE$_1$ and additionally discloses 11-deoxy-17-phenyl-18,19,20-trinor-PGE$_2$.

SUMMARY OF THE INVENTION

This invention provides novel 11-deoxy-17-phenyl prostaglandin analogs. This invention further provides esters and pharmacologically acceptable salts of these analogs. This invention further provides novel processes for preparing these analogs and their esters and salts. Further, this invention provides novel intermediates useful in the preparation of said analogs and, their esters, and their salts.

Particularly, the present invention comprises:
a compound of the formula

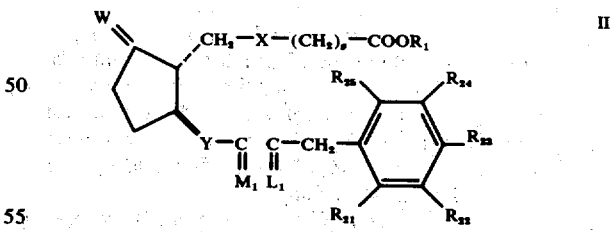

or a mixture comprising that compound and the enantiomer thereof;
a compound of the formula

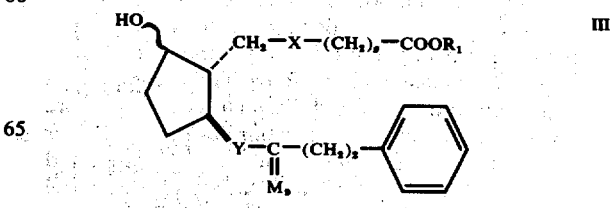

or a mixture comprising that compound and the enantiomer thereof;
a compound of the formula

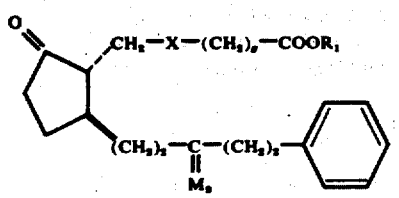

or a mixture comprising that compound and the enantiomer thereof;
wherein g is 3 to 5, inclusive;
wherein W is

or

wherein X is —$CH_2CH_2$— or cis-CH=CH—;
wherein Y is —$CH_2CH_2$— or trans-CH=CH—;
wherein $L_1$ is

or a mixture of

and

wherein $R_3$ and $R_4$ are hydrogen or methyl, being the same or different;
wherein $M_1$ is

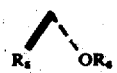

or

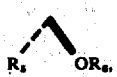

wherein $R_5$ and $R_6$ are hydrogen or methyl, with the proviso that $R_5$ is methyl only when $R_6$ is hydrogen and $R_6$ is methyl only when $R_5$ is hydrogen;
wherein $M_9$ is

or

wherein $R_1$ is hydrogen, alkyl of 1 to 12 carbon atoms, inclusive, cycloalkyl of 3 to 10 carbon atoms, inclusive, aralkyl of 7 to 12 carbon atoms, inclusive, phenyl, phenyl substituted with 1, 2, or 3 chloro or alkyl of 1 to 3 carbon atoms, inclusive, or a pharmacologically acceptable cation;

Wherein $R_{21}$, $R_{22}$, $R_{23}$, $R_{24}$ and $R_{25}$ are hydrogen, fluoro, chloro, trifluoromethyl, alkyl of 1 to 4 carbon atoms, inclusive, or —$OR_8$ wherein $R_8$ is alkyl of 1 to 3 carbon atoms, inclusive, with the proviso that at least 2 of $R_{21}$, $R_{22}$, $R_{23}$, $R_{24}$, and $R_{25}$ are hydrogen, and not more than 2 of $R_{21}$, $R_{22}$, $R_{23}$, $R_{24}$, and $R_{25}$ are chloro, fluoro, trifluoromethyl or —$OR_8$, with the further proviso that $R_{21}$, $R_{22}$, $R_{23}$, $R_{24}$, and $R_{25}$ are all hydrogen only when at least one of $R_3$, $R_4$, $R_5$, and $R_6$ is methyl.

Formulas II–IV include separate C-15 isomers wherein $M_1$ or $M_9$ is either

or

i.e., where —$OR_5$ is in either the natural (alpha or L) or epi (beta or D) configuration, wherein the terms D and L relate to the absolute configuration of D- or L- glyceraldehyde using the standard Fischer convention. See M. Hamberg, Advan. Bio. Sci. 9, 847 (1973).

Formula II represents substituted 11-deoxy-17-phenyl PG analogs of this invention wherein at least a hydrogen at C-15 or C-16 is replaced by methyl or at least one of the phenyl hydrogens is replaced by chloro, fluoro, trifluoromethyl, lower alkyl of lower alkoxy. Accordingly, formula II provides 11-deoxy-15-methyl-17-phenyl-PG type compounds when $R_5$ is methyl. Further, formula II provides 11-deoxy-17-phenyl-PG-type, 15-methyl ethers when $R_6$ is methyl. In addition, 11-deoxy-16-methyl-17-phenyl-PG-type compounds and 11-deoxy-16,16-dimethyl-17-phenyl-PG-type compounds are provided when either one and only one of $R_3$ and $R_4$ are methyl or both $R_3$ and $R_4$ are methyl, respectively. Substituted phenyl compounds are also provided. For example, when $R_{22}$ or $R_{24}$ is trifluoromethyl and the remaining moieties of the group consisting of $R_{21}$, $R_{22}$, $R_{23}$, $R_{24}$, and $R_{25}$ are hydrogen, there are provided 11-deoxy-17-(m-trifluoromethylphenyl)-PG-type compounds.

Further, the C-15 hydroxy or alkoxy group is attached to the side chain in the alpha configuration, i.e. wherein $M_1$ is

when the PG-type compound possesses the same absolute configuration at the C-15 position as $PGE_1$ obtained from mammalian tissues.

However, also included in this invention are the 15-epimer compounds wherein $M_1$ is

These compounds are hereinafter identified as "15-epi" compounds. For example, in Formula II when $M_1$ is

11-deoxy-15-epi-17-phenyl-PG-type compounds are described.

For all of the novel PG-type compounds of this invention in the hydroxy or alkoxy substituted side chain, the terminal n-propyl group of the parent 11-deoxy prostaglandins is replaced by a phenyl or substituted phenyl. Accordingly, the name of each of the novel prostaglandin analogs of this invention includes the designation "18,19,20-trinor" to indicate the absence of these three carbon atoms.

Further, included in the scope of this invention are those 11-deoxy-PG-type compounds wherein the carboxy terminated side chain contains 7 carbon atoms as in $PGE_1$ obtained from the mammalian tissues. Further, contained herein are those carboxy terminated side chains wherein 8 or 9 carbon atoms, are present. The names of these compounds include either "2a-homo" or "2a,2b-dihomo" respectively.

The formulas II-IV plus their respective mirror images describe a racemic mixture within the scope of this invention. For convenience hereinafter such a racemic compound is designated by the prefix "racemic" ("rac" or "dl") before its name. When that prefix is absent, the optically active compound represented by formulas II-IV is designated. Combination of the Enantiomers corresponding to each of the formulas herein, other than in equal quantities yields mixtures other than racemic mixtures.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, y-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of

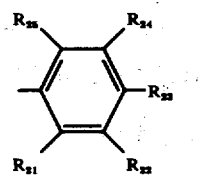

wherein $R_{21}$ to $R_{25}$ are as defined above, are phenyl, (o-, m-, or p-)tolyl, (o-, m-, or p-(ethylphenyl, 2-ethyl-p-tolyl, 4-ethyl-o-tolyl, 5-ethyl-m-tolyl, (o-, m-, or p-(propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-2,4-, 2,5-, 2,6-, 3,4-, or 3,5-)-dichlorophenyl, 4-chloro-3-fluorophenyl, (3-, or 4-)chloro-2-fluorophenyl, o-, m-, or p-trifluoromethyl, (o-, m-, or p-)methoxyphenyl, (o-, m-, or p-)ethoxyphenyl, (4- or 5-)-chloro-2-methoxyphenyl, and 2,4-dichloro(5- or 6-)methoxyphenyl.

The novel PG analogs of this invention correspond to the prostaglandins described above, in that the novel PG analogs exhibit prostaglandin-like activity. Specifically, the 11-deoxy-PGE-type compounds of this invention correspond to the PGE compounds described above, in that these novel PGE-type compounds are useful for each of the above described purposes for which the PGE compounds are used, and are used in the same manner as the PGE compounds, as described above. Further, the 11-deoxy-$PGF_\alpha$-type compounds of this invention correspond to the $PGF\alpha$ compounds described above, in that these novel $PGF\alpha$ -type compounds are useful for each of the above-described purposes for which the $PGF\alpha$ compounds are used and are used in the same manner as the $PGF\alpha$ compounds, as described above. Finally, the 11-deoxy $PGF\beta$ -type compounds of this invention correspond to the $PGF\beta$ compounds described above, in that these novel $PGF\beta$ -type compounds are useful for each of the above described purposes for which the $PGF\beta$ compounds are used, and are used in the same manner as the $PGF\beta$ compounds, as described above.

The prostaglandins described above are all potent in causing multiple biological responses even at low doses. Moreover, for many applications these prostaglandins have an inconveniently short duration of biological activity. In striking contrast, the novel prostaglandin analogs of this invention are substantially more selective with regard to potency in causing prostaglandin-type responses, and have a substantially longer duration of biological activity.

Accordingly, each of the novel prostaglandin analogs of this invention is surprisingly and unexpectedly more useful than one of the corresponding prostaglandins, described above, for at least one of the pharmacological purposes indicated for the corresponding prostaglandin, because each of the novel prostaglandin analogs has a different and narrower spectrum of biological potency than the corresponding prostaglandin, and therefore is more specific in its activity and causes smaller and fewer undesired side effects than when the corresponding prostaglandin is used for the same purpose. Moreover, because of its prolonged activity, fewer and smaller doses of the novel prostaglandin analog are frequently used to obtain the desired result.

Another advantage of the novel compounds of this invention, especially the preferred compounds defined hereinbelow, compared with the known prostaglandins, is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

The novel prostaglandin analogs of this invention are less sensitive to dehydration or rearrangement than 11-hydroxy PG's or PG-type compounds, and consequently possess a surprising and unexpected increase in chemical stability and duration of shelf life.

As discussed above, the novel compounds of this invention are administered in various ways for various purposes: e.g., intravenously, intramuscularly, subcutaneously, orally, intravaginally, rectally, buccally, sublingually, topically, and in the form of sterile implants for prolonged action. For intravenous injection of infusion, sterile aqueous isotonic solutions are preferred. For that purpose, it is preferred because of increased water solubility that $R_1$ in the novel compounds of this invention be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublinqual administration. For rectal or vaginal administration, suppositories prepared are known in the art are used. For tissue implants, a sterile tablet or silicone rubber capsule or other object containing or impregnated with the substance is used.

The novel PG analogs of this invention are used for the purposes described above in the free acid form, in ester form, in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel PG analogs of this invention compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4,-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)-aminomethane, N-phenylethanolamine, N-)p-tert-amylphenyl)-diethanolamine, galactamine, N-methylgycamine, N-methyglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

To obtain the optimum combination of biological response specificity, potency, and duration of activity, certain compounds within the scope of this invention are preferred.

For example, those compounds wherein g is 3 or 5 are preferred. Those compounds wherein g is 3 are especially preferred. With respect to the group consisting of $R_{21}$, $R_{22}$, $R_{23}$, $R_{24}$, and $R_{25}$, those compounds are preferred wherein $R_{21}$ - $R_{25}$ are all hydrogen, or one and only one of $R_{21}$ - $R_{25}$ is not hydrogen, and that element of the group not hydrogen is chloro, fluoro, or trifluoromethyl. Those compounds wherein $R_5$ and $R_6$ are both hydrogen are preferred when at least one of $R_3$ and $R_4$ are methyl. Those compounds in which $R_3$ and $R_4$ are both hydrogen are preferred when one of $R_5$ and $R_6$ is methyl.

Reference to Charts A, B, C, and D will make clear the processes by which the novel compounds of this invention are prepared. With respect to Chart A g, $L_1$, $M_1$, and $R_1$ are as defined above. $R_7$ is

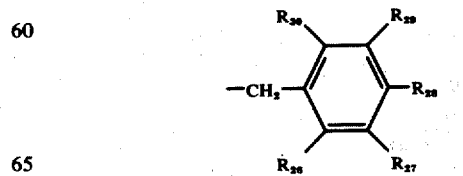

wherein $R_{26}$, $R_{27}$, $R_{28}$, $R_{29}$, and $R_{30}$ are hydrogen, chloro, fluoro, trifluoroethyl, alkyl of one to 4 carbon atoms, inclusive, or —OR$_6$, wherein R$_6$ is alkyl of one to 3 carbon atoms, inclusive, with the proviso that at least two of R$_{26}$, R$_{27}$, R$_{28}$, R$_{29}$, and R$_{30}$ are hydrogen, and not more than two are chloro, fluoro, trifluoromethyl, or —OR$_6$; M$_5$ is
or a mixture of
and
M$_6$ is
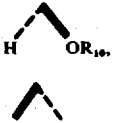
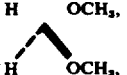
or a mixture of
and
Chart A
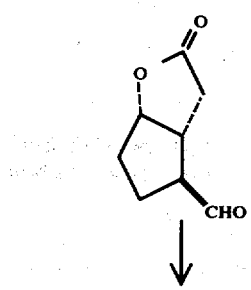
V
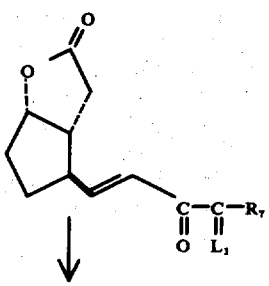
VI
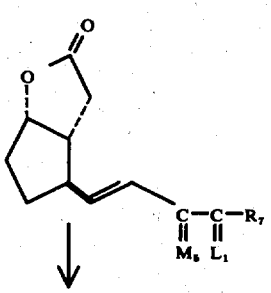
VII
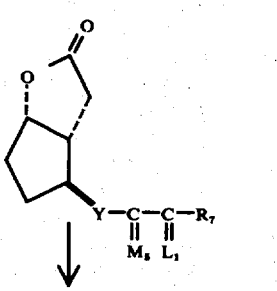
VIII
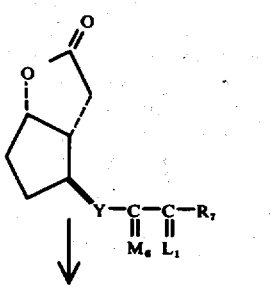
IX
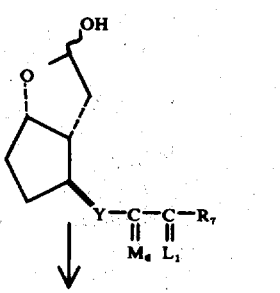
X -continued
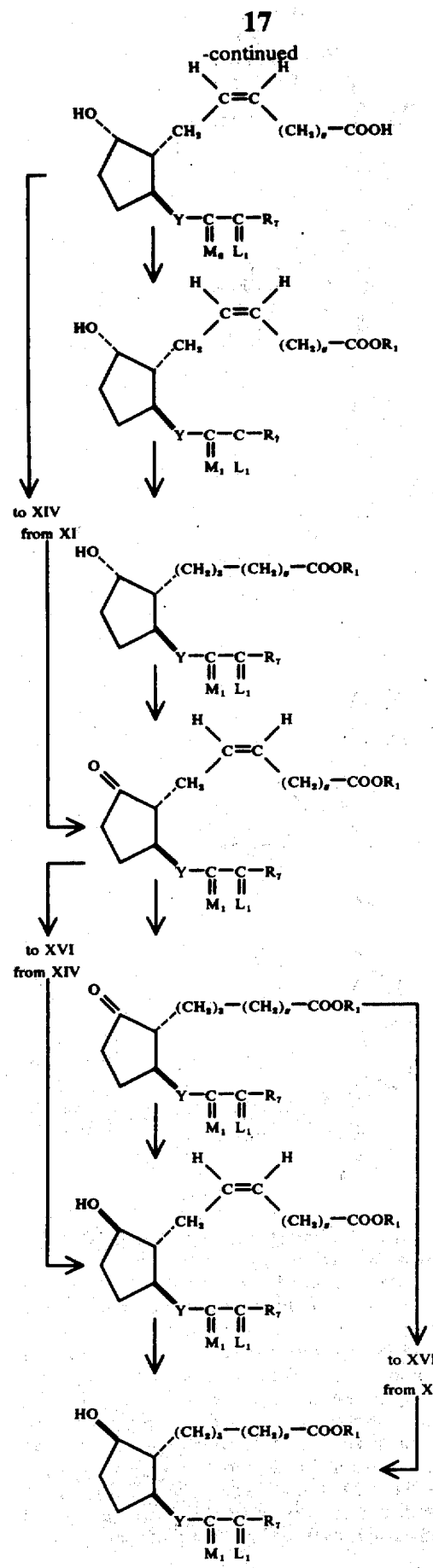
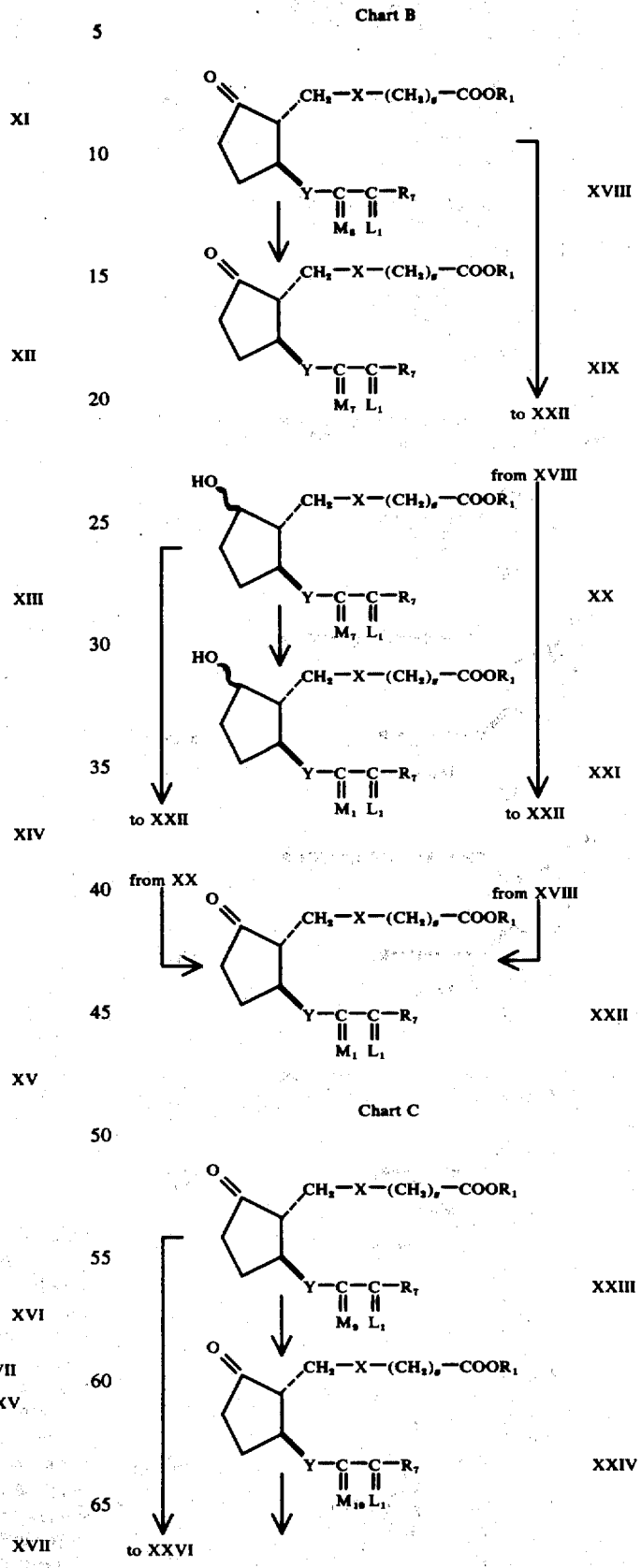

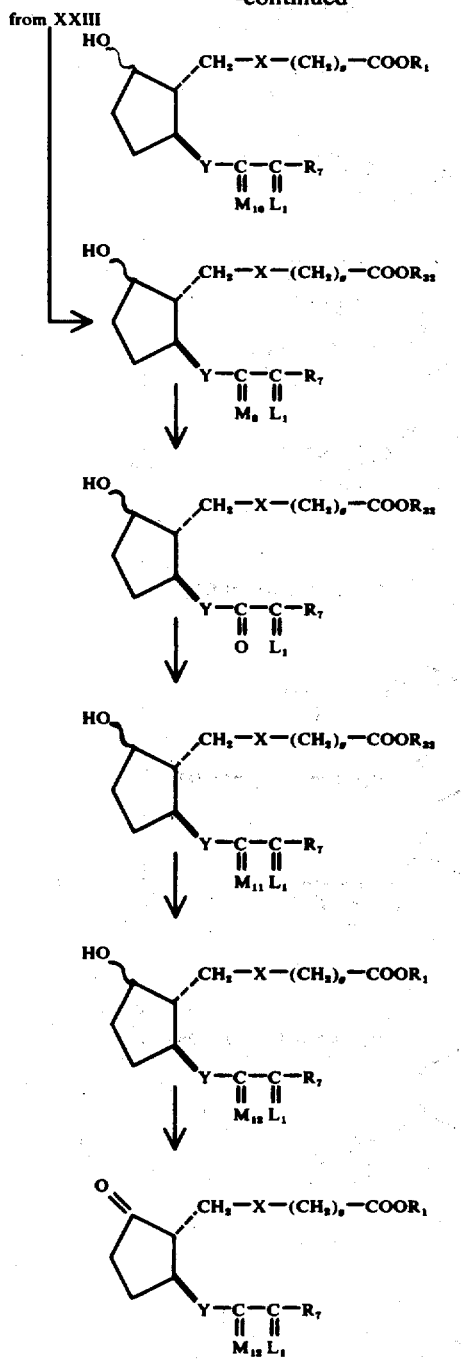

Chart D

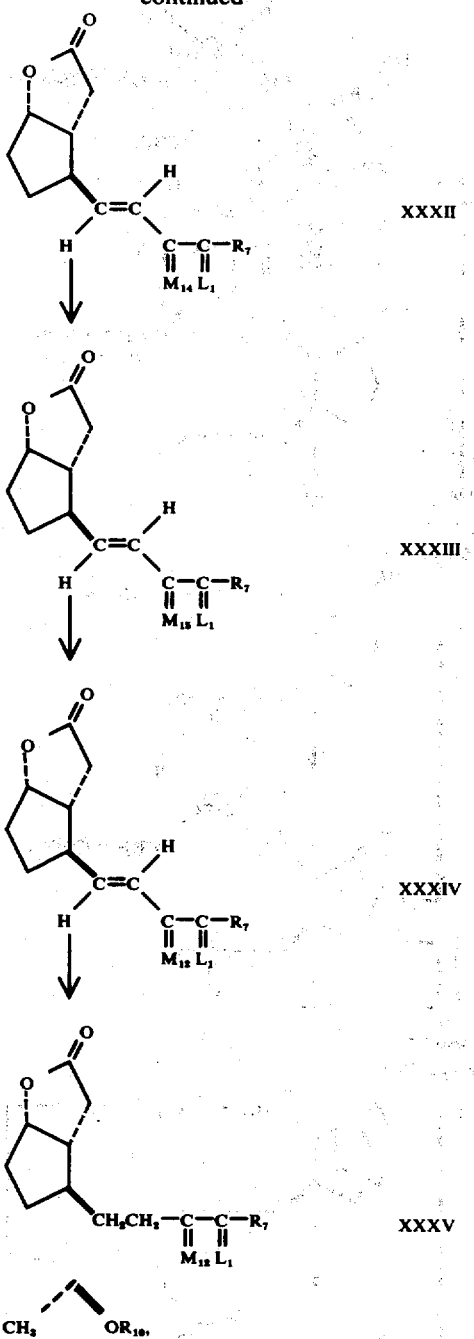

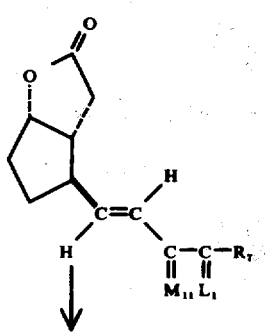

wherein $R_{10}$ is a blocking group, which is defined as any group which replaces hydrogen of the hydroxy groups, which is neither attacked nor is reactive to reagents used in the respective transformations herein to the extent that the hydroxy group is, and which is subsequently replaceable by hydrogen at a later stage in the preparation of the protaglandin-type products. Several blocking groups are known in the art, e.g. tetrahydropyranyl and substituted tetrahydropyranyl (see Corey, Proceedings of the Robert A. Welch Foundation Conferences on Chemical Research, XII, Organic Synthesis, pp. 51–79 (1969)). Those blocking groups which have been found useful include (a) tetrahydropyranyl; (b) tetrahydrofuranyl; or (c) a group of the formula

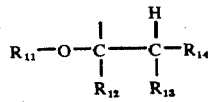

wherein R₁₁ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{12}$ and $R_{13}$ are the same or different, being hydrogen, alkyl of one to 4 carbon atoms, inclusive, phenyl or phenyl substituted with one, 2, or 3 alkyl of one to 4 carbon atoms, inclusive, or when $R_{12}$ and $R_{13}$ are taken together, —(CH₂)$_b$— or —(CH₂)$_c$—O—(CH₂)$_d$—wherein $b$ is 3, 4, or 5, $c$ is one, 2, or 3, and $d$ is one, 2, or 3 with the proviso that $c$ plus $d$ is 2, 3, or 4, and wherein $R_{14}$ is hydrogen or phenyl.

The formula V aldehyde is known in the art. See Crabbe, et al. Tetrahedron Letters, No. 2, 115 (1972). The procedure described in Chart A is performed by methods known in the art. See E. J. Corey, et al., Journal of the American Chemical Society 91, 5675 (1969). The formula V compound may be prepared on the optically active form as depicted by formula V, or as a mixture of the formula V compound and its enantiomer. For the production of the formula II-V optically active compounds of this invention, the compound depicted by formula V, being optically active, is used.

The formula VI compound is obtained by Wittig alkylation of the formula V compound using the sodio derivative of an appropriate 2-oxo phosphonate having the formula

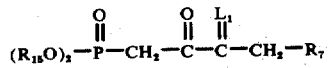

wherein $R_7$ and $L_1$ are as defined above and $R_{15}$ is alkyl of 1 to 8 carbon atoms, inclusive, especially methyl. The phosphonates are prepared and used by methods known in the art. The trans enone lactone (formula VI) is obtained stereospecifically (see D. H. Wadsworth, et al., Journal of Organic Chemistry, vol. 30, pg. 680 (1965)). Conveniently, the appropriate phenyl substituted aliphatic acid ester is condensed with dimethyl methylphosphonate in the presence of n-butyllithium. For this purpose, acids of the general formula

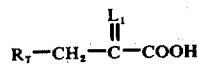

are used in the form of lower alkyl esters, preferably methyl or ethyl. For this purpose, methyl esters are readily formed from the acids by reacton with diazomethane. These aliphatic acids with phenyl substitution within the scope of $R_7$ as defined above, are known in the art or can be prepared by methods known in the art.

The formula VII compound wherein M₅ is

or

is obtained as a mixture of alpha and beta hydroxy isomers by non-ethylenic reduction of the formula VI compound. For this reduction, use is made of any of the known ketonic carbonyl reducing agents which do not reduce ester or acid groups or carbon-carbon double bonds. Examples of such reducing agents are the metal borohydrides especially sodium, potassium, and zinc borohydrides, lithium (tri-tert-butoxy)aluminum hydride, metal trialdoxy borohydrides, e.g. sodium trimethoxy borohydride, lithium borohydride, diisobutylaluminum hydride, and when carbon-carbon double bond reduction is not a problem the boranes, e.g. bis-3-methyl-2-butyl borane. For the production of the natural configuration prostaglandin at C-15, the alpha form of the formula VII compound is separated from the beta isomer by silica gel chromatography. Methods known in the art are used. Separation of these C-15 epimers may alternatively be performed on the final prostaglandin-type products. The formula VII compound wherein M₅ is

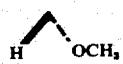

or

is obtained by non-ethylenic reduction of the formula VI compound and separation of the resulting C-15 hydroxy epimers, as described above, followed by methylation of the side chain hydroxy of the 15α- or 15β-hydroxy compound so formed. For this purpose, diazomethane may be employed, preferably, in the presence of a Lewis acid, e.g. boron trifluoride etherate, aluminum chloride, or fluoroboric acid. See Fieser et al., "Reagents for Organic Synthesis", John Wiley and Sons, Inc., New York (1967), pg. 191. The reaction is carried out by mixing a solution of the diazomethane in an inert solvent, preferably diethyl ether, with the free hydroxy compound. Generally the reaction proceeds at about 25° C. Another method for alkylation of the side chain hydroxy is by reaction with an alcohol in the presence of boron trifluoride etherate. Thus, methanol and trifluoride etherate yield the methyl ether. The reaction is done at about 25° C. and conveniently followed with thin layer chromatography (TLC).

Another method for alkylation of the side chain hydroxy is by reaction of a methyl halide e.g. methyl iodide in the presence of a metal oxide or hydroxide, e.g. barium oxide, silver oxide, or barium hydroxide. The reactants are preferably stirred together and maintained at temperatures of 25° -75° C.

Still another method is by first converting the hydroxy to mesyloxy (i.e. methanesulfonate) or tosyloxy (i.e. toluenesulfonate), and thereafter transforming the mesyloxy or tosyloxy to the—OCH₃ moiety by reaction with a metal alkoxide, e.g. potassium tert butoxide. The mesylate or tosylate is prepared by reaction of the free hydroxy compound with either methanesulfonyl chloride or toluenesulfonyl chloride in pyridine. Thereafter the mesylate or tosylate is mixed with appropriate pottasium or sodium methoxide in pyridine, the reaction proceeding smoothly at about 25° C. This method is however not preferred, since its employment often results in epimerization of the methoxy.

The formula VII compounds M₅ is a mixture of

and

is prepared by reacting the formula VI compound with a conventional Grignard reagent, CH₃MgHal, wherein Hal is chloro, bromo, or iodo. Alternatively, the alkylation proceeds by reaction of the formula VI compound with trimethylaluminum, as known in the art. Separation of the 3-methyl epimers does proceed as described in Chart D. However, for compounds wherein Y is trans-CH=CH—, such separation is preferably effected on the PG-type methyl ester product, as discussed below.

Thus, there are prepared the compounds according to formula VII.

The formula VIII compound wherein Y is —CH₂CH₂— is prepared from the formula VII compound by catalytic hydrogenation of the C₁₃-C₁₄ double bond. This hydrogenation is accomplished by methods known in the art, i.e. the use of metal catalysts under a hydrogen atmosphere. The formula IX compound is prepared from the formula VIII compound by replacing any free hydroxy hydrogens of the formula VIII compound with blocking groups. When the blocking group is tetrahydropyranyl or tetrahydrofuranyl, the appropriate reagent, e.g. 2,3-dihydropyran or 2,3-dihydrofuran, is used in an inert solvent such as dichloromethane, in the presence of an acid condensing agent such as p-toluenesulfonic acid or pyridine hydrochloride. The reagent is used in large excess, preferably 1.2 to 100 times theory. The reaction is carried out at about 20°-50° C.

When the blocking group is of the formula

as defined above, the appropriate reagent is a vinyl ether, e.g. isobutyl vinyl ether or any vinyl ether of the formula wherein R₁₁, R₁₂, R₁₃, and R₁₄ are as defined above; or an unsaturated cyclic or heterocyclic compound, e.g. 1-cyclohexen-1-yl methyl ether

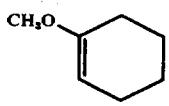

or 5,6-dihydro-4-methoxy-2H-pyran

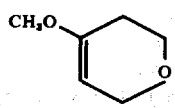

See C. B. Reese et al., J. Am. Chem. Soc. 89, 3366 (1967). The reaction conditions for such vinyl ethers and unsaturates are similar to those for dihydropyran above.

The formula X compound is prepared from the formula IX compound by reduction of the lactone of formula IX to a lactol. This reduction is carried out by use of a nonethylenic reducing agent. For this purpose, diisobutylaluminum hydride is used as is known in the art. The reaction is preferably carried out at -60° to -70° C. The formula XI compound is prepared from the formula X compound by a Wittig alkylation using the appropriate (ω-carboxyalkyl(triphenylphosphonium bromide, HOOC—(CH₂)$_g$—CH₂—P(C₆H₅)₃Br, and sodio dimethylsulfinylcarbanide. The phosphonium compounds are known in the art or are readily available, i.e., by reaction of an ω-bromo aliphatic acid and triphenylphosphine.

The formula XII PGF₂α -type compound is prepared from the formula XI compound when M₆ is a mixture of

by hydrolysis of the blocking groups under mild acidic conditions as is known in the art, followed by methyl esterification, as described hereinbelow, separation of the C-15 epimers using procedures known in the art (silica gel chromatography), and transformation of the carboxy ester to an R₁ moiety by the methods and procedures hereinbelow described.

The formula XI compound wherein M₆ is

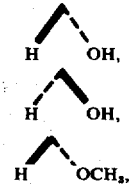

or

yields the corresponding formula XII compound by the above described procedure, except that the methyl esterification and the separation of the C-15 epimers is omitted.

The formula XIII compound is prepared from the formula XII compound hydrogenation using one or two mole equivalents of hydrogen per mole equivalent of prostaglandin-type compound. When Y is trans-CH=CH— in the formula XII compound and the formula XIII PGF₁α -type compound is desired, hydrogenation with one mole equivalent of hydrogen is accomplished using a catalyst comprising palladium-on-charcoal or rhodium-on-aluminum under a hydrogen atmosphere at atmospheric or low pressure. See, for example E. J. Corey et al., Journal of the American Chemical Society, 91, 567 (1969) and B. Samuelsson, Journal of Biological Chemistry 239, 4091 (1964). For preparation of the 13,14-dihydro-PGE₁-type compounds from the formula XII compound wherein Y is trans-CH=CH— two mole equivalents of hydrogen are used as described above. For the preparation of the PGE$_1$-type compounds from the formula XII compound wherein Y is trans-CH=CH—, it is preferred that a metal catalyst (i.e. palladium) be used which selectively effects the reduction of the cis-5,6-unsaturation in the presence of trans-13,14-unsaturation. Mixtures of products obtained upon hydrogenation herein are conveniently separated by use of silica gel chromatography as is known in the art. The formula XIV compound is prepared from the formula XI compound by oxidation of the C-9 hydroxy to a C-9 oxo group by use of an oxidizing reagent as is known in the art. Thereafter the preparation of the formula XIV compound from the formula XI proceeds as is described above for the preparation of the formula XII compound from the formula XI compound, e.g. for production of the 15-alkyl type compounds hydrolysis of the blocking groups is followed by methyl esterification and separation of the C-15 epimers before transformation of the carboxy ester to the more general R$_1$ moiety. For those compounds wherein the C-15 epimers have been separated at the lactone stage, the hydrolysis of the blocking groups is followed by transformation of the carboxy hydrogen to an R$_1$ moiety.

The formula XV compound is then prepared from the formula XIV compound by hydrogenation of the formula XIV compound by the methods and procedures described hereinabove for the preparation of the formula XIII compound from the formula XII compound.

The formula XVI compound is prepared from the formula XIV compound by a ring carbonyl reduction using, ring carbonyl reduction reagents of known prostaglandin derivatives as is known in the art. See, for example, Bergstrom, et al., Arkiv. Kemi. 19, 563 (1963) Octa. Chem. Scand. 16, 969 (1962) and British Specification No. 1,097,533. any reducing agent is used which does not react with carbon-carbon double bonds or with ester groups. Preferred reagents are lithium (tri-tert-butoxy)aluminum hydride, the metal borohydrides, especially sodium, potassium, and zinc borohydrides, the metal trialkoxy borohydrides, e.g. sodium trimethoxyborohydride. The beta hydroxy epimer is then separated from the alpha hydroxy epimer by methods known in the art. See, for reference Bergstrom, et al., cited above Granstrom, et al., Journal of Biological Chemistry 240, 457 (1965), and Green, et al., Journal of Lipid Research 5, 117 (1965). Alternate separation methods are partition chromatographic procedures, both normal and reversed phase, preparative thin layer chromatography, and counter current distribution procedures. The formula XVII compound is then prepared from the formula XV compound by a ring carbonyl reduction, using the methods and procedures described herein for the preparation of the formula XVI compound from the formula XIV compound.

Accordingly, by the procedures of Chart A there are prepared the PGE, PGF$\alpha$, and PGF$\beta$ -type compounds of this invention.

Chart B provides an alternate method whereby the PGE, PGF$\alpha$, and PGF$\beta$ compounds of this invention are prepared from corresponding PGA-type compounds known in the art, or prepared by methods known in the art. With respect to Chart B, g, X, Y, L$_1$, R$_1$, and R$_7$ are as defined above. M$_7$ is

or

wherein R$_{16}$ is hydrogen or methyl and R$_{17}$ is methyl or a blocking group, with the proviso that R$_{16}$ is methyl only when R$_{17}$ is a blocking group and R$_{17}$ is methyl only when R$_{16}$ is hydrogen. This blocking group functions to prevent attack on the hydroxy group by subsequent reagents, especially the oxidizing reagent for transforming the C-9 hydroxy to a C-9 oxo. This blocking group is further required to be replaceable by hydrogen at a later stage in the preparation of the prostaglandin-type products. The blocking groups which have been found useful include alkanoyl, blocking groups according to R$_{10}$ as defined above, silyl groups of the formula —Si(G)$_3$ wherein G is alkyl of one to 4 carbon atoms, inclusive, phenyl, phenyl substituted with one or 2 fluoro, chloro, or alkyl of 1 to 4 carbon atoms, inclusive, aralkyl of 7 to 12 carbon atoms, inclusive. M$_8$ is

or

wherein R$_{18}$ is hydrogen or methyl and R$_{19}$ or R$_{31}$, with the proviso that R$_{18}$ is hydrogen. R$_{31}$ and and R$_{19}$ is methyl only when R$_{18}$ is hydrogen. R$_{31}$ is hydrogen, alkanoyl of 2 to 8 carbon atoms, inclusive, or a blocking group according to R$_{10}$. With respect to Chart B the formula XIX compound is reduced to form the formula XX compound by use of an alkali metal borohydride. This reduction reduces ring unsaturation as well as reducing the 9-oxo to a 9-hydroxy. This reaction is carried out at about −20° C. and is ordinarily complete within several minutes.

The formula XIX compound is prepared from the formula XVII compound by replacing any free hydroxy hydrogen atom at the C-15 position with blocking groups according to R$_{17}$.

In the use of blocking groups according to R$_{17}$, methods known in the art are employed. Thus, for example, when an alkanoyl blocking group is used the appropriate anhydride or acid chloride e.g. acetic anhydride or acetic chloride, is reacted with the prostaglandin-type compound in the presence of a tertiary amine such as pyridine, triethylamine, and the like. The reaction is carried out under a variety of conditions using procedures known in the art. Generally mild conditions are employed, e.g., 20°–60° C., and the reaction proceeds by contacting the reactants in a liquid medium, e.g., excess pyridine or an inert solvent such as benzene, toluene or chloroform. The acylating agent is used in either a stoichiometric amount or in slight stoichiometric excess. If the acyl chloride is not available, it may be prepared from the corresponding acid and phosphorus pentachloride or thionyl chloride as is known in the art.

When the blocking group is silyl of the formula -Si(G)₃, the silyl derivative is prepared by procedures know in the art. See, for example, Pierce, "Silylation of Organic compounds", Pierce Chemical Co., Rockford, Ill. (1968). The necessary silylating agents for these transformations are known in the art or are prepared by methods known in the art. See, for example, "Silicones and Other Organic Silicone compounds", Reinhold Publishing Corp., New York, N. Y. (1959). These reagents are used in the presence of a tertiary base, such as pyridine and temperatures in the range of about 0–50° C. Examples of trisubstituted monochlorosilane suitable for this purpose include chlorotrimethylsilane, chlorotriisobutyl silane, chlorotriphenylsilane, chloro tris (p-chlorophenyl)silane, chlorotrim-tolylsilane, and tribenzylfluorosilane. Alternatively, the chlorosilane is used with the corresponding disilizanes. Examples of other silylating agents suitable of performing the silyl derivatives include pentaethylsilylamine, N-trimethylsilyldiethylamine, 1,1,1-triethyl-trimethylsilylamine, and N-triisopropyl-1,1,1-trimethylsilylamine, 1,1-tributyl-N,N-dimethylsilylamine, N,N-dibutyl-1,1,1-trimethylsilylamine, 1-isobutyl-N,N-1,1-tetramethylsilylamine, N-benzyl-N-ethyl-1,1,1-trimethylsilylamine, N,N,1,1-tetramethyl-1-phenylsilylamine, N,N-diethyl-1,1-dimethyl-1-phenylsilylamine, N,N-diethyl-1methyl-1,1-diphenylsilylamine, N,N-dibytl-1,1,1-triphenylsilylamine, and 1-methyl-N,N,1,1-tetraphenylsilylamine.

For blocking groups within the scope of R₁₇ and the scope of R₁₀ the appropriate reaction conditions and reagents as specified hereinabove are employed.

The formula XXI compound is prepared from the formula Xx compound by hydrolysis of the blocking groups as described hereinabove, followed by separation of the C-9epimers also as described herein.

The formula XXII compound is then prepared from the formula XX compound or from the formula XVIII compound. When prepared from the formula XX compound the preparation proceeds first by oxidation of the 9-hydroxy to a 9-oxo compound, followed by hydrolysis of the blocking group. A useful oxidizing reagent for this purpose is the Jones reagent, i.e. acidified chromic acid. See Journal of the Chemical Society 39 (1947). A slight stoichiometric excess beyond the amount necessary to oxidize the secondary hydroxyl group is used. Acetone is a suitable diluent for this purpose. Reaction temperatures at least as low as 0° C. should be used. Preferred reaction temperatures are in the range −50° C. An especially useful reagent for this purpose is the Collins reagent i.e. chromium troxide in pyridine. See J. C. Collins, et al., Tetrahedron Letters 3363 (1968). Dichloromethane is a suitable diluent for this purpose. Reaction temperatures of below 37° C. should be used. Preferred reaction temperatures are in the range of −10° to +10° C. The oxidation proceeds rapidly and is usually complete in about 2 to 5 minutes. The product may be isolated by conventional means, e.g. chromatographic methods.

Examples of other oxidation reagents useful for this transformation are silver carbonate on celite (Chem. Communications 1102 (1969)), mixtures of chromium trioxide and pyridine (Journal of the American Society 75, 422 (1953)), and Tetrahedron, 18, 1351 (1962)), t-butyl chromate in pyridine (Biochemical Journal, 84, 195 (1962)), mixtures of sulfur trioxide in pyridine and dimethyl sulfoxide (Journal of the American Chemical Society, 89, 5505 (1967)), and mixtures of dicyclo-hexylcarbodiimide and dimethyl sulfoxide, (Journal of the American Chemical society, 87, 5661 (1965)).

Hydrolysis of the blocking groups proceeds as described above. Silyl groups are readily removed by prior art procedures known to be useful for transforming silyl ethers and silyl esters to alcohols and carboxylic acids, respectively. See, for example, Pierce, cited above, especially page 447 thereof. Alternatively, the formula XXII compound is prepared from the formula XVIII compound by catalytic hydrogenation, whereby ring unsaturation is removed without effecting olefinic chain unsaturation. For this purpose 5 percent palladium or rhodium catalysts on carbon alumina or other suitable supports are used. Reductions are carried out at any number of solvents e.g. ethyl acetate methanol, ethanol, diethyl ether, and temperatures of −30° to +50° C. and at pressures of about 1 atmosphere to 3.5 kg./cm. Also, the M₇moiety is transformed into the M₁moiety by hydrolytic methods described herein.

Chart C provides yet another method whereby novel prostaglandin-type compounds of this invention may be prepared. With respect to Chart C, g, X, Y, L₁ M₁, R₁, and R₇ are as defined hereinabove. M₁₀ is

or

M₁₁ is a mixture of

and

M₁₂ is

or

and R₃₂ is alkyl of one to 12 carbon atoms, inclusive, cycloalkyl of 3 to 10 carbon atoms, inclusive, aralkyl of 7 to 12 carbon atoms, inclusive, phenyl, phenyl substituted with 1, 2, or 3 chloro or alkyl of one to 3 carbon atoms, inclusive. by the procedure of Chart C an alternative method is provided whereby the 15-methyl ether and 15-methyl type compounds of this invention are prepared. The formula XXIII compound has been prepared by the procedures descirbed above.

The formula XXIV compound is prepared from the formula XXIII compound by reaction of the formula XXIII compound with a methyl halide. For example, methyl iodide in the presence of silver oxide in refluxing benzene is advantageously employed. When R₁ is hydrogen in the formula XXIII compound methyl esterification is also accomplished by reaction with the methyl hilide. Accordingly, the preparation of the formula XXIV compound wherein R₁ is hydrogen would require saponification of the methyl ester, using the methods described hereinbelow. The formula XXV compound is then prepared from the formula XXIV compound by carbonyl ring reduction as described hereinabove.

The formula XXVI compound is also prepared from the formula XXIII compound by carbonyl ring reduction as described hereinabove. The formula XXVII compound is then prepared from the formula XXVI compound by oxidation of the C-15oxo. Oxidation reagent such as 2,3-dichloro-5,6-dicyano-1,4-benzoquinone, activated magnesium dioxide, or nickel are advantageously employed. See for reference Fieser, et al., Reagents for Organic Synthesis, John Wiley and Sons, Inc., N.Y., N.Y., especially pages 215, 637, and 731.

The formula XXVIII compound is then prepared from the formula XXVII compound by alkylation of the C-15 oxo. For this Grignard reagent of the formula $CH_3MgHal$, wherein Hal is chloro, bromo, or iodo may be employed. Alternatively trimethylaluminum may be used for this alkylation. The procedure of alkylation by use of the Grignard or trimethylaluminum is described hereinabove. The formula XXIX compound is then prepared from the formula XXVIII compound by separation of the C-15 epimers. This epimeric separation is accomplished here by transforming the $R_{22}$ moiety into a methyl ester, separating the PG-type methyl ester so formed, and transforming the carboxy methyl ester into the $R_1$ moiety. The formula XXIX compound is available in either the 9α-hydroxy or 9β-hydroxy configuration. Separation of these 9-hydroxy epimers is conveniently accomplished by the methods described hereinabove for preparation of the formula XXV - XXVII compounds.

The formula XXX is then prepared from the formula XXIX compound by oxidation of the 9-hydroxy to a 9-oxo group. The C-15 hydroxy of the formula XXIX compound may be protected by a blocking group, according to $R_{10}$, prior to oxidation. When used, the blocking group is subsequently hydrolyzed, under acidic conditions, as described hereinabove. Accordingly, there are prepared in formulas XXIX and XXX the novel prostaglandin-type compounds of this invention.

Chart D provides a preferred porcess whereby the 15-alkyl-13,14-dihydro-PG-type compounds of this invention are prepared. $R_7$ and $L_1$ are as defined above. $M_{11}$ is a mixture of

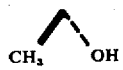

and

$M_{12}$ is

or

$M_{14}$ is a mixture of

and

wherein $R_{22}$ is benzoyl. $M_{15}$ is

or

wherein $R_{22}$ is benzoyl.

The formula XXXII compound is prepared from the formula XXXI compound by benzoylation. Benzoylation is accomplished, for example, by reaction of the formula XXXI compound with benzoyl chloride. The reaction proceeds at 0° C. to completion in about 15 min. The formula XXXIII compound is prepared from the formula XXXII compound by silica gel chromatographic separation.

The formula XXXIV compound is then prepared from the formula XXXIII compound by hydrolysis of the benzoyl group. Hydrolysis is advantageously accomplished by treatment of the formula XXXIII compound with an alkaline metal methoxide in methanol, quenched by the addition of sodium bisulfate.

The formula XXXV compound is then prepared from the formula XXXIV compound by catalytic hydrogenation. Methods described hereinabove, i.e. the use of metal catalysts, are employed. Finally the formula XXXV lactone is transformed into corresponding PG-type compounds following the procedure of Chart A.

In all of the above-described reactions the products are separated by conventional means from the starting materials and impurities, for example by silica gel chromatography monitored by thin-layer chromatography (TLC).

Optically active compounds are obtained from optically active intermediates according to the process steps of Charts A, B, and C. When racemic intermediates are used in reactions corresponding to the processes of Chart A-D, inclusive, and racemic products are obtained, these racemic products may be used in their racemic form or, if preferred, they may be resolved as optically active isomers by procedures known in the art.

For example, when final compounds II–IV are free acids, the dl form thereof is resolved into the d and l forms by reacting said free acid by known general procedures with an optically active base, e.g., brucine or strychnine, to give a mixture of two diastereoisomers which are separated by known general procedures, e.g., fractional crystallization, to give the separate diastereoisomeric salts. The optically active acids of formulas II–IV are then obtained by treatment of the salt with an acid by known general procedures.

It is preferred that the formula V compound be used in the optically active form which will lead to an 11-deoxy prostaglandin analog of the natural configuration. For this purpose, there is provided for resolving a racemic mixture of an oxo compound of the formula

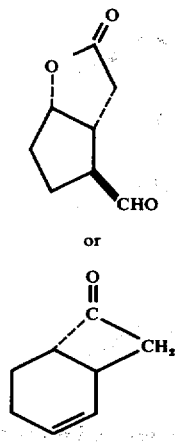

V or

XLIV and of the mirror image thereof, which comprises the steps of a. convertint the oxo compound by reaction with an optically active ephedrine to a mixture of oxazolidine diastereomers, b. separating at least one oxazolidine diastereomer from said mixture, c. hydrolyzing said oxazolidine to free the optically active oxo compound, and d. recovering said optically active oxo compound.

In carrying out the resolution of the formula XLIV ketone, there is prepared an oxazolidine by reaction of the ketone with an optically active ephedrine, e.g. d- or l- ephedrine, or d- or l-pseudoephedrine. Approximately equimolar quantities of the reactants are employed in a solvent such as benzene, isopropyl ether, or dichloromethane. The reaction proceeds smoothly over a wide range in temperature, for example 10° to 80° C., although for some reactants the range 20° to 30° C. is preferred for convenience. The reaction occurs quickly, within minutes, whereupon the solvent is removed, preferably under vacuum. The product consists of the diastereomers of the ketoneephedrine product, i.e. the oxazolidines. At least one of the diastereomers is separated by methods known in the art, including crystallization and chromatography. In this instance, crystallization is used as the preferred method. Repeated recrystallization of the thus-obtained solid oxazolidine from a suitable solvent, e.g., isopropyl ether, yields one of the diastereomers in substantially pure form. The oxazolidine is then hydrolyzed by procedures known in the art to release the ketone.

The mother liquor from the recrystallized diastereomer contains the optical isomer having opposite configuration. A preferred method for isolating this second diastereomer, however, is to prepare the oxazolidine of the racemic ketone using ephedrine of the opposite configuration to that first employed above, and thereafter recrystallizing as above. Finally, hydrolysis and recovery yield the resolved formula XLIV ketone in opposite configuration to that first obtained above.

Each optically active ketone can be converted to an aldehyde of the formula

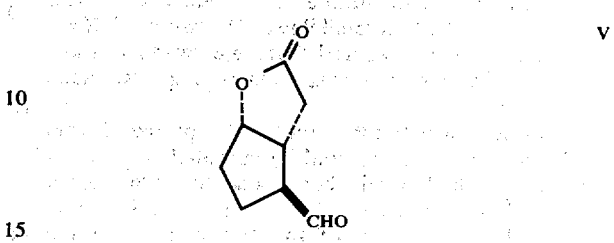

V or the mirror thereof, theof, using the procedures of Corey et al., Tetrahedron Letters 49, 4753 (1971). That ketone is especially useful which yields the formula V aldehyde which produces the 11-deoxy prostaglandin analogs having the natural configuration.

Likewise, the above process of resolution applied to the racemate containing the formula V aldehyde yields the optically active formula V aldehyde which produces the 11-deoxy prostaglandin analogs having the natural configuration.

As discussed above, the processes herein described inclusive, lead variously to acids ($R_1$ is hydrogen) or to esters.

When the alkyl ester has been obtained and an acid is desired, saponification procedures, as known in the art for F-type prostaglandins are employed.

Alternatively, enzymatic processes for transformation of esters to their acid forms are used by methods known in the art. See for reference E. G. Daniels, Process For Producing An Esterase, U.S. Pat. No. 3,761,356.

When an acid has been prepared and an alkyl, cycloalkyl, or aralkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2ethylhexane, and diazodecane, for example, gives the ethyl, butyl and 2-ethylhexyl and decyl esters, respectively. Similarly, diazocyclohexane and phenyldiazomethane yield cyclohexyl and benzyl esters respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N.Y., Y., Vol. 8, pp. 389–394 (1954).

An alternative method for alkyl, cycloalkyl or aralkyl esterification of the carboxyl moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tertbutyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The phenyl and substituted phenyl esters of this invention are prepared by methods known in the art. For example, the prostaglandin-type free acid may be silylated by methods known in the art, thereby protecting the free hydroxy groups. Since the silylation may transform the carboxy acid, moiety, —COOH, into a silyl ester derivative, a brief treatment of the silylated compound with water may be necessary to transform the silylated compound into free acid form. This free acid may then be reacted with oxalyl chloride to provide an acid chloride. The acid chloride may be esterified by reacting it with phenol or the appropriate substituted phenol to give a silylated phenyl or substituted phenyl ester. Finally, the silyl groups are replaced by free hydroxy moieties by hydrolysis under acidic conditions. For this purpose dilute acetic acid may be advantageously used.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

DESCRIPTION OF THE PREFERRED EMBODIMENTS

The invention can be more fully understood by the following examples and preparations:

All temperatures are in degrees centigrade. IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer on deuterochloroform solutions with tetramethylsilane as an internal standard.

Mass spectra are recorded on an CEG model 1108 Double Focusing High Resolution Mass Spectrometer or an LKB Model 9000 Gas-Chromatograph-Mass Spectrometer. Trimethyl silyl derivatives are used, except where otherwise specified.

The collection of chromatographic eluate fractions starts when the eluant front reaches the bottom of the column.

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

"Skellysolve-B" (SSB) refers to mixed isomeric hexanes.

Silica gel chromatography, as used herein, is understood to include elution, collection of fractions, and combination of those fractions shown by TLC (thin layer chromatography) to contain the desired product free of starting material and impurities.

Melting points (MP) are determined on a Fisher-Johns melting point apparatus.

DDQ refers to 2,3-dichloro-5,6-dicyano-1,4-benzoquinone.

THF refers to tetrahydrofuran.

Specific Rotations, [α], are determined for solutions of a compound in the specified solvent at ambient temperature with a Perkin-Elmer Model 141 Automatic Polarimeter.

PREPARATION 1

Dimethyl 3,3-dimethyl-2-oxo-4-phenylbutylphosphonate

A. To a solution of 101.2 g. of diisopropylamine in 125 ml. of tetrahydrofuran under nitrogen is added dropwise at 0° C. with cooling an equal molar amount of n-butyllithium in hexane. To this solution is added dropwise with cooling 46.5 ml. (44 g.) of isobutyric acid. The mixture is stirred at 0° C. for 90 min. and is then cooled to −15° C. Benzyl chloride (60 ml.) is added with stirring in such a rate as to maintain the reaction temperature below −5° C. The mixture is then stirred at ambient temperature for 4 hr. The mixture is diluted with diethyl ether and cold dilute hydrochloric acid. The organic layer is washed, dried, concentrated, and the residue distilled. The product, 48 g., exhibits boiling point 107°–110° C.

B. A mixture of the reaction product of Step A above (2,2-dimethyl-3-phenylpropionic acid) and 82 g. of thionyl chloride is heated with stirring for 2 hr. The mixture is concentrated, dry benzene is added, and the mixture is then concentrated a second time to remove all traces of thionyl chloride. Distillation of the residue yields 48.2 g. of a product.

C. To a solution of 63 g. of dimethyl methylphosphonate in 600 ml. of tetrahydrofuran under nitrogen atmosphere at −75° C. is added with stirring 312 ml. of 1.6 M n-butyllithium in hexane. The condition is regulated so as to maintain a reaction temperature below −55° C. Ten minutes after the addition, 48.2 g. of the reaction product of step B above (2,2-dimethyl-3-phenylpropionyl chloride) in 15 ml. of tetrahydrofuran is added dropwise. The dropwise addition is regulated so as to maintain a reaction temperature below −60° C. The mixture is stirred at −75° C. for 2 hr. and at ambient temperature overnight. Acetic acid (20 ml.) is added and the tetrahydrofuran is removed by distillation. The residue is shaken with diethyl ether-methylene chloride (3:1, by volume) and dilute sodium bicarbonate solution. The organic layer is washed with saturated saline and then dried and concentrated. The residue is recrystallized in diethyl ether to give 54 g. of the title compound of this preparation. Melting point 49°-51° C.

Following the procedure of Preparation 1, but using in place of the benzyl chloride of step A of Preparation 1 the following substituted benzyl chlorides there are obtained the corresponding dimethyl 3,3-dimethyl-2-oxo-4-(substituted phenyl)butylphosphonates:

| Preparation | Substituted benzyl chloride |
|---|---|
| 2 | Cl (ortho), ClCH₂ |
| 3 | Cl (meta), ClCH₂ |
| 4 | ClCH₂—(para)—Cl |
| 5 | F (ortho), ClCH₂ |
| 6 | F (meta), ClCH₂ |
| 7 | ClCH₂—(para)—F |
| 8 | CF₃ (ortho), ClCH₂ |
| 9 | CF₃ (meta), ClCH₂  |
| 10 | ClCH₂—(para)—CF₃  |

Following the procedure of Preparation 1, but using propionic acid in place of isobutyric acid, there is obtained dimethyl 3-methyl-2-oxo-4-phenylbutyl phosphonate.

Following the procedure of Preparation 1, but using the propionic acid in the manner described above and the substituted benzyl chlorides used in Preparation 2-10, there are prepared the corresponding dimethyl 3-methyl-2-oxo-4-(substituted phenyl)butyl phosphonates.

Further, following the procedure of Preparation 1, but using acetic acid in place of isobutyric acid, there is prepared dimethyl 2-oxo-4-phenyl-butylphosphonate. Also using acetic acid as described above and using substituted benzyl chlorides in place of benzyl chloride as used in Preparation 1, there are prepared by the procedure of Preparation 1 the corresponding dimethyl-2-oxo-4-(substituted phenyl)butylphosphonates.

PREPARATION 11

5α-hydroxy-2β-(3α-hydroxy-5-phenyl-trans4-pentenyl)-1α-cyclopentaneacetic acid, γ lactol, tetrahydropyranyl ether (Formula X: Y is trans-CH=CH—, M₆ is

```

H   OTHP,
```

L₁ is

```

H   H,
``` and R₇ is

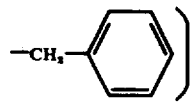

and its 3-beta hydroxy epimer.

Refer to Chart A.

A. A solution of 11.4 g. of dimethyl 2-oxo-4-phenyl-butylphosphonate in 15 ml. of tetrahydrofuran is added with stirring to a solution of potassium t-butoxide in 200 ml. of tetrahydrofuran under nitrogen at 0°-5° C. The mixture is stirred for about 1.5 hr. To the stirred mixture is added 30 ml. of 5α-hydroxy-2β-carboxaldehyde-1α-acetic acid γ lactone in 50 ml. of benzene. This mixture is stirred at ambient temperature for 2 hr. and thereafter 2 ml. of acetic acid is added. The mixture is then concentrated and the residue eluted with diethyl ether-methylene chloride (3:1) and washed with cold dilute hydrochloric acid, dilute sodium bicarbonate, and saturated saline. This mixture is then dried and concentrated.

B. Purification of the crude product above is accomplished by column chromatography using 1 kg. of silica gel and elution with ethyl acetate and Skellysolve B (1:1). The pure compound is recovered from the appropriate fractions as determined by thin layer chromatography. A stirred mixture of 3.88 g. of zinc chloride and 75 ml. of dry dimethyl ether in ethylene glycol (glyme) under nitrogen is cooled in an ice bath while 1.21 g. of sodium borohydride is added. The ice bath is removed. The mixture is stirred at ambient temperature for 16 hr. The mixture is then cooled in an ice-methanol bath to less than −15° C. A solution of 1.89 g. of 5α-hydroxy-2β-(3-oxo-5-phenyl-trans-1-pentenyl)-1α-cyclopentaneacetic acid, γ lactone, the product of step A above in 40 ml. of glyme is added during a 20 min. period. The mixture is then stirred at 2° C. for 5 hr. 9 ml. of water is then added to the mixture. After adding 200 ml. of ethyl acetate, the mixture is filtered and the filter cake is washed with 200 ml. of ethyl acetate. The combined filtrate and washing is washed with 100 ml. of water and 100 ml. of brine and dried with magnesium sulfate. Evaporation of the solvent under reduced pressure yields 2.7 g. of oil. The oil is chromatographed on 200 g. of silica gel. Eluting with 5 percent acetone in methylene chloride, 100 ml. fractions are collected. Fractions shown by silica gel thin layer chromatography to contain the product are segregated from those containing the 3-beta epimer.

The total yield of both epimers is 748 mg. The 3α-isomer shows mass spectral peaks at 286, 268, 240, 195, 187, 181, 169, 161, 135, 105, 92, and 91. Infrared absorptions are observed at 3430, 1765, 1600, 1495, 1455, 1205, 1165, 1035, 1010, 975, 900, 750, and 705 cm.$^{-1}$. NMR peaks are observed at 1.2–2.9, 3.9–4.3, 4.8–5.2, 5.5–5.68, and 7.28.

C. A mixture of 7.38 g. of 5α-hydroxy-2β-(3α-hydroxy-5-phenyl-trans-1-pentenyl)-1α-cyclopentaneacetic acid, γ-lactone, the product of step B above, 1.09 g. of dihydropyran, a few crystals of pyridine hydrochloride, and 30 ml. of methylene chloride is stirred under nitrogen for 22 hr. Evaporation of the solvent under reduced pressure at 40° C. yields an oil containing some solid. To a stirred solution of the above material in 50 ml. of dried toluene under nitrogen cooled in an ice-methanol bath is added 42 ml. of 10 percent diisobutylaluminum hydride in toluene during 30 min. The mixture is stirred an additional hour while cooled. The cooling bath is removed. A mixture of 14 ml. of tetrahydrofuran and 9 ml. of water is added dropwise during 20 min. The mixture is allowed to warm to room temperature, the solid separates and is removed by filtration. The filter cake is washed well with benzene. The combined filtrate and washings are washed with brine and dried with magnesium sulfate. Evaporation of the solvent under reduced pressure yields 1.03 g. of the lactol of this preparation as an oil. The 3β-epimer is obtained using the 3β starting material from part B of this preparation and employing the procedure of this paragraph.

PREPARATION 12

5α-Hydroxy-2β-(3α-methoxy-5-phenyl-trans-1-pentenyl)-1α-cyclopentane acetic acid, γ-lacto (Formula X: Y is trans-CH=CH—, M₆ is

L₁ is

and R₇ is

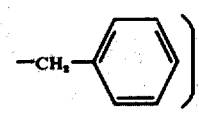

and its 3β-methoxy epimer.

Refer to Chart A.

Following the procedure of Preparation 11, parts A and B the formula V aldehyde is converted to the formula VIII 3α-hydroxy lactone. The formula VIII 3α-hydroxy lactone (1.91 g.), silver oxide (4.08 g.), and 50 ml. of methyl iodide is stirred and heated at reflux for 68 hr. Chloroform (25 ml.) is added and the mixture is filtered. The filtrate is concentrated to an oil which is taken up in chloroform (50 ml.). The solution is washed with brine, dried over magnesium sulfate, and concentrated to an oil. Separation by silica gel chromatography, eluting with 40 percent ethyl acetate in Skellysolve B, and combining those fractions shown by thin layer chromatography to contain the product free of starting material and impurities, yields the formula IX lactone.

Finally, following the procedure of Preparation 11, step C, but omitting the etherification step, there is prepared the title compound.

The 3β-epimer is prepared from the 3β-starting material.

PREPARATION 13

5α-Hydroxy-2β-[(3RS)-3-methyl-3-hydroxy-5-phenyl-trans-1-pentenyl]-1α-cyclopentaneacetic acid, γ-lactol (Formula X: Y is trans-CH=CH—, M₆ is a mixture of

and

L₁ is

and R₇ is

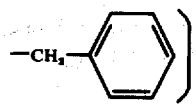

Following the procedure of Preparation 11, part A, there is prepared the formula VI 5α-hydroxy-2β-(3-oxo-5-phenyl-trans-1-pentenyl)-1α-cyclopentaneacetic acid, γ-lactone.

To a stirred solution of 0.3 g. of 5α-hydroxy-2β-(3-oxo-5-phenyl-trans-1-pentenyl)-1α-cyclopentaneacetic acid, γ-lactone in 25 ml. of benzene under nitrogen is added 1.35 ml. of a 1.69 molar solution of trimethylaluminum in toluene. A yellow color develops immediately, The solution becomes colorless. After 4.5 hr., an additional 1.5 ml. of the trimethylaluminum solution is added. The reaction is then monitored by thin layer chromatography. When substantially all the starting material has been exhausted, the reaction is quenched by an addition of 30 ml. of ammonium chloride, which is cautiously added dropwise. A solid separates. The mixture is stirred thoroughly to insure that all the trimethylaluminum has decomposed. Then 50 ml. of diethyl ether is added and the mixture is filtered. The filter cake is washed with diethyl ether. The combined filtrate washings are shaken and the layers are separated. The aqueous layer is extracted with 25 ml. of diethyl ether the combined organic layers are dried with magnesium sulfate. Evaporation of the solvent under reduced pressure at 40° C. yields an oil. The oil is chromatographed and the mixture of 3(RS)-methyl lactones is recovered as shown by thin layer chromatography.

The lactone of the proceeding paragraph is then etherified and reduced according to the procedure of Preparation 11, step C. The title compound results.

Following the procedure of Preparations 11, 12, and 13, but using (2-oxo-3-methyl or 3,3-dimethyl-4-phenylbutyl)-phosphonates there are obtained the corresponding lactols: 5α-hydroxy-2β-[(3R)-3-methoxy-4-methyl- or 4,4-dimethyl-5-phenyl-trans-1-pentenyl]-1α-cyclopentaneacetic acid, γ-lactol, tetrahydropyranyl ether and its 3S-methoxy epimer; and 5α-hydroxy-2β-[3(RS)-3-methyl-3-hydroxy-4-methyl- or 4,4-dimethyl-5-phenyl-trans-1-pentenyl]-1α-cyclopentaneacetic acid, γ-lactol, tetrahydropyranyl ether.

Further, following the procedure of Preparations 11, 12, and 13, but using the 3,3-dihydro-, 3-methyl-, or 3,3-dimethyl aralkyl phosphonates described above there are prepared the corresponding γ-lactols.

2-Oxo-3-methyl4-phenyl-butyl phosphonates and the corresponding substituted phenyl phosphonates, exist in either of two optically active (+ or −) forms or racemic (dl) mixtures. An optically active phosphonate is obtained by starting with an appropriate optically active aralkyl acid. Methods of resolving these acids are known in the art, for example, by forming salts with an optically active base such as brucine, separating the resulting diastereomers, and recovering the acids.

For the purposes of this invention the 4-methyl lactone and lactol intermediates prepared from the above phosphonates and the 16-methyl PG-type products herein are used in either the optically active or epimerically mixed form.

Thus, there are prepared the following compounds

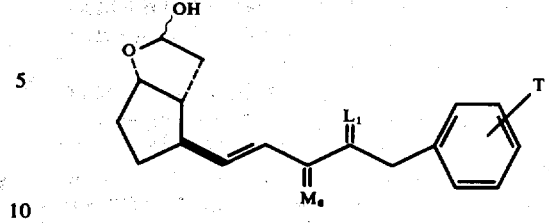

wherein $M_6$ and $L_1$ are defined above and T is hydrogen, chloro, fluoro, or trifluoromethyl.

PREPARATION 14

(6-Carboxyhexyl)triphenylphosphonium bromide, $Br(C_6H_5)_3$—$P(CH_2)_6$—COOH

Triphenylphosphine (156 g.) and 7-bromoheptanoic acid (115 g.) are heated in 125 ml. of benzene at reflux for 18 hr. The crystalline product is filtered off, washed with benzene, and recrystallized from methanol diethyl ether. Melting point 185°–187° C.

EXAMPLE 1

11-Deoxy-18,19,20-trinor-17-phenyl-$PGF_{2\alpha}$ (Formula XII: g is 3, $R_1$ is hydrogen, Y is trans-CH=CH—, $M_1$ is

$L_1$ is

and $R_7$ is

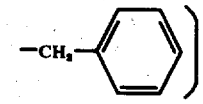

and its 15-epimer.

A. A mixture of 0.84 g. of 57 percent sodium hydride in mineral oil and 30 ml. of dry dimethylsulfoxide under nitrogen is heated at 60° to 65° C. for 1.5 hr. The brown-red solution is cooled to 24° C. Then 4.43 g. of (4-carboxybutyl)triphenylphosphonium bromide is added. The mixture is stirred for 15 min. A solution of the lactol of Preparation 11 and 30 ml. of dimethylsulfoxide is added dropwise during 5 min. The mixture is stirred for 18 hr. After addition of 15 ml. of benzene the mixture is cooled in an ice bath while a solution of 3.54 g. of potassium bisulfate in 40 ml. of water is slowly added. The mixture is diluted with 200 ml. of water and extracted with benzene. The organic extracts are washed with 100 ml. of water and dried using magnesium sulfate. Evaporation of the solvent at reduced pressure yields 4.0 g. of a yellow oil. The oil is slurried with ether. Upon standing a solid separates. The solid is removed by filtration and washed with diethyl ether. Evaporation of the diethyl ether from the filtrate washing yields 2.34 g. of the yellow oil. The oil is chromatographed on a 200 g. column of acid washed silica gel. Elution with 30 percent ethyl acetate and Skellysolve B yields 11-deoxy-18,19,20-trinor-17-phenyl-PGF$_{2\alpha}$, 15-tetrahydropyranyl ether.

B. The reaction product of part A above (0.41 g.), 10 ml. of tetrahydrofuran, 10 ml. of water, and 20 ml. of acetic acid are heated to 42° C. for 3 hr. After addition of 40 ml. of water the mixture is frozen in a dry ice-acetone bath and thereafter freeze-dried until the mixture reached room temperature. The oil obtained is then chromatographed on a 40 g. column of acid washed silica gel. Elution with 35 percent ethyl acetate in Skellysolve B yields the title compound as a pale yellow oil. The mass spectrum shows peaks at 372, 354, 336, 267, 249, 245, 227, 221, 206, 133, 119, and 105. The infrared spectrum shows absorptions at 3400, 2640, 1710, 1600, 1495, 1455, 1405, 1300, 1240, 1165, 1120, 1030, 970, 750, and 700 cm.$^{-1}$. NMR peaks are observed at 1.1 to 2.9, 3.9–4.35, 4.9–5.2, 5.3–5.68, and 7.98.

Using as starting material the 3$\beta$-hydroxy lactol the corresponding 15-epimer of the title compound is obtained.

Following the procedure of Example 1, part A, but using in place of the lactol of Preparation 11 the lactol of Preparation 12 there is prepared the corresponding 11-deoxy-18,19,20-trinor-17-phenyl-PGF$_{2\alpha}$, 15-methyl ether. The 15-epimer of this compound is likewise prepared using the corresponding 3$\beta$-methoxy lactol as described above.

EXAMPLE 2

11-Deoxy-15-methyl-17-phenyl-18,19,20-trinor-PGF$_{2\alpha}$ (Formula XII: g is 3, R$_1$ is hydrogen, Y is trans-CH=CH—, M$_1$ is

L$_1$ is

and R$_7$ is

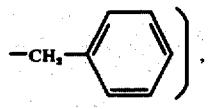

its 15-epimer, and the methyl esters thereof.

Refer to Chart A.

Following the procedure of Example 1, parts A and B, but using in place of the 3-hydroxy lactol of Preparation 11 the 3(RS)-methyl lactol of Preparation 13, there is prepared 11-deoxy-15(RS)-15-methyl-17-phenyl-18,19,20-trinor-PGF$_{2\alpha}$. The methyl ester is then prepared by reaction of this compound with diazomethane in a mixture methanol and diethyl ether (1:1). After the mixture has stood at about 25° C. for 5 min., it is concentrated under reduced pressure to yield 11-deoxy-15(RS)-15-methyl-17-phenyl-18,19,20-trinor-PGF$_{2\alpha}$, methyl ester.

Silica gel chromatography is then used to separate the 15-epimers. Those fractions shown by thin layer chromatography to contain essentially 15-epimerically pure 15(R) and 15(S) title compounds are combined to form 11-deoxy-15-methyl-17-phenyl-18,19,20-trinor-PGF$_{2\alpha}$ and 11-deoxy-15-epi-15-methyl-17-phenyl-18,19,20-trinor-PGF$_{2\alpha}$ as methyl esters.

C. The methyl esters of part B above are saponified as follows:

A solution of 2 g. of the methyl ester in 20 ml. of methanol is cooled to 0° C. and then treated dropwise under nitrogen with 12 ml. of 10 percent aqueous sodium hydroxide. The mixture is then allowed to warm to room temperature and stir for 2 hr. After removal of the methanol by evaporation under reduced pressure, the residue is diluted with 50 ml. of water and then extracted with methylene chloride. The aqueous layer is then cooled with ice, treated with 24 ml. of 2 molar aqueous sodium bisulfate solution, and thereafter extracted with ethyl acetate. The combined extracts are then washed with brine, dried over anhydrous sodium sulfate, and concentrated. The crude product is then chromatographed on 150 g. of silica gel eluting with ethyl acetate and Skellysolve B (1:1). Fractions containing the free acid are combined to yield the title compound in free acid form.

Following the procedure of the preceding paragraph there is likewise obtained the 15-epi-15-methyl compound of this example. Following the procedure of Examples 1 and 2, using the 4-methyl-5-phenyl or 4,4-dimethyl-5-phenyl lactols described in Preparations 11, 12, and 13 there are prepared the corresponding 11-deoxy-16-methyl- or 16,16-dimethyl-17-phenyl-18,19,20-trinor-PGF$_{2\alpha}$ type free acids or methyl esters wherein the C-15 moiety is

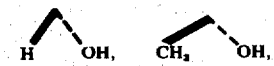

or

and their respective 15-epimers.

Following the procedure of Examples 1 and 2, but using the susbstituted 5-phenyl lactols of Preparations 11, 12, and 13, there are prepared the corresponding 17-substituted phenyl-PGF$_{2\alpha}$ -type compounds of this invention, in both free acid and methyl ester form wherein the C-15 substituents are described in the preceeding paragraph and the C-16 carbon is optionally substituted with 1 or 2 methyl groups, e.g. 16-methyl or 16,16-dimethyl compounds.

PREPARATION 15

11-Deoxy-18,19,20-trinor-17-phenyl-PGE$_2$ (Formula XIV: g is 3, R$_1$ is hydrogen, Y is trans-CH=CH—, M$_1$ is

L$_1$ is

and $R_7$ is

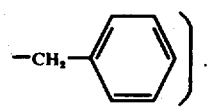

its 15-epimer and the methyl esters thereof.

A stirred solution of 340 mg. of the reaction product of Example 1, part A, 11-deoxy-17-phenyl-18,19,20-trinorPGF$_{2\alpha}$, 15-tetrahydropyranyl ether, in 20 ml. of acetone is cooled in an ice methanol bath while 1 ml. of Jones reagent (2.67 mmol. of $CrO_3$) is added during 1 min. the mixture is then stirred an additional 30 min. at −30° C. Thereafter 1 ml. of isopropanol is added and the mixture is stirred at −20° C. for an additional 10 min. The mixture is then diluted with 100 ml. of water and extracted thrice with 75 ml. of diethyl ether. The combined extracts are washed with brine and dried with magnesium sulfate. Evaporation of the solvent under reduced pressure at 40° C. yields 0.51 g. of an oil.

B. A mixture of the oil in 10 ml. of tetrahydrofuran, 10 ml. of water, 20 ml. of acetic acid is heated at 43° C. for 3.5 hr. After addition of 40 ml. of water, the mixture is frozen in an dry-ice acetone bath and then freeze dried until the mixture reaches room temperature. The oil is then chromatographed on a 40 g. column of acid washed silica gel. The column is eluted with 25 percent ethyl acetate in Skellysolve B. Those fractions shown by silica gel thin layer chromatography to contain the 15α-title compounds are combined, yielding 96 mg. of the product as an oil. The mass spectrum shows peaks at 352, 334, 265, 261, 247, 243, 191, 187, 135, 109, 105, 96, and 91. The infrared spectrum shows absorptions at 3400, 2640, 1730, 1600, 1495, 1450, 1405, 1275, 1230, 1155, 1055, 1030, 975, 750, and 700 cm.$^{-1}$. NMR peaks are observed at 1.2–3.0, 3.4–4.0, 5.3–5.6, 5.6–5.8, 5.9–6.2, and 7.2δ.

Use of the 15β-tetrahydropyranyl ether in place of the compound of Example 1, part B yields the corresponding 15β product. Further, the methyl ester of either 15-epimeric configuration is obtained by reaction of the PGE-type compound with diazomethane according to the procedure of Example 2, part B.

Following the procedure of the Preparation 15, but using in place of 11-deoxy-17-phenyl-18,19,20-trinor-PGF$_{2\alpha}$, 15-tetrahydropyranyl ether the other PGFα -type compounds described following Example 1, in Example 2, and following Example 2 there are obtained the corresponding 16-methyl-or 16,16-dimethyl-17-phenyl or 17-substituted phenyl-PGE$_2$-type compounds of this invention wherein the C-15 carbon is substituted optionally with methyl or methoxy. Further, the compounds of the preceding sentence are obtained in either free acid or methyl ester form according to the procedure described above.

PREPARATION 16

11-Deoxy-18,19,20-trinor-17-phenyl-PGE$_1$

Formula XV: wherein g is 3, $R_1$ is hydrogen, Y is trans-CH=CH, $M_1$ is

$L_1$ is

and $R_7$ is

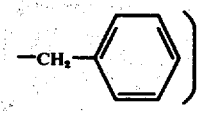

and its 15β-epimer.

A mixture of the formula XIV 11-deoxy-17-phenyl-18,19,20-trinor-PGE$_2$ (Preparation 15, 220 mg.), 5 percent rhodium-on-alumina catalyst (40 mg.) and 16 ml. of ethyl acetate is stirred under 1 atmosphere of hydrogen at about 0° C. until substantially all of the starting material is used, as shown by thin layer chromatography. Thereafter the resulting mixture is filtered to remove the catalyst employed above. After all catalyst is removed by this filtration process the preparation proceeds by causing the mixture to be concentrated under reduced pressure. The residue thereof is chromatographed over silica gel, eluting with the upper layer of a mixture of ethyl acetate, acetic acid, Skellysolve B, and water (90:20:50:100). Those fractions shown by thin layer chromatography to contain the title compound free of starting material and impurities are combined and concentrated to yield the title compound.

Following the procedure of Preparation 16, but using in place of the PGE$_2$ starting material of this preparation its 15β-epimer there is prepared the corresponding 15-epi-PGE$_1$-type compound.

Following the procedure of Preparation 16, but using in place of the PGE$_2$ novel-type compounds of this preparation or its 15-epimer the corresponding PGE$_2$-type methyl ester and its 15-epimer, there are obtained the corresponding PGE$_1$-type methyl esters.

Further, following the procedure of Preparation 16, but using in place of the C-15 unsubstituted PGE$_2$-type compound of Preparation 16 and above, the 15-methyl and 15-methyl ether PGE$_2$-type compounds described above, there are obtained the corresponding 15-methyl and 15-methyl ether PGE$_1$-type compounds of either 15-epimeric configuration in both free acid and methyl ester form. Further, following the procedure of Preparation 16 but using in place of the C-16 unsubstituted PGE$_2$-type compound therein the 16-methyl or 16,16-dimethyl-PGE$_2$-type compounds described above there are obtained the corresponding 16-methyl or 16,16-dimethyl-PGE$_1$-type compounds of this invention. Finally, following the procedure of Preparation 16, but using the various 17-substituted phenyl PGE$_2$-type compounds described above there are obtained the corresponding 17-substituted phenyl-PGE$_1$-type compounds. The compounds in this paragraph represent the novel PGE$_1$-type compounds of this invention.

EXAMPLE 3

11-Deoxy-17-phenyl-18,19,20-trinor-13,14-dihydro-PGE$_1$ (Formula XV: g is 3, R$_1$ is hydrogen, Y is —CH$_2$CH$_2$—, M$_1$ is

L$_1$ is

and R$_7$ is

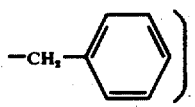

and its 15-epimer.

A solution of 11-deoxy-17-phenyl-18,19,20-trinor-PGE$_2$ (Preparation 20, 100 mg.) in 10 ml. of ethyl acetate is shaken with hydrogen at about 1 atmosphere of pressure at 25° C. in the presence of a 5 percent palladium-on-charcoal catalyst (15 mg.). Two equivalents of hydrogen are used, whereupon the hydrogenation is stopped and the catalyst is removed by filtration. The filtrate is concentrated under reduced pressure and the residue is chromatographed under reduced pressure and the residue is chromatographed on silica gel eluting with ethyl acetate-Skelly-solve B. Those fractions shown by thin layer chromatography to contain the title compound free from starting material and impurities are combined and concentrated to yield the title compound.

Following the procedure described in the preceding paragraph, but using the 15-epimer in place of the PGE$_2$-type compound therein, there is obtained the corresponding 15-epi-13,14-dihydro-PGE$_1$-type compound.

Following the procedure of Example 3, but using in place of the PGE$_2$-type compound therein the various PGE$_2$-type compounds described following Preparation 15 there are obtained the corresponding 13,14,-dihydro-PGE$_1$-type compounds. Accordingly, there are obtained 13,14-dihydro-PGE$_1$-type compounds wherein 15-methyl or 15-methoxy, 16-methyl or 16,16-dimethyl, or 17-chloro-, fluoro-, or trifluoromethyl-phenyl substitutents are present.

EXAMPLE 4

11-Deoxy-17-phenyl-18,19,20-trinor-PGF$_{2\beta}$ (Formula XVI: g is 3, R$_1$ is hydrogen, Y is trans-CH=CH—, M$_1$ is

L$_1$ is

and R$_7$ is

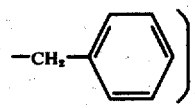

A solution of sodium borohydride (300 mg.) in 6 ml. of ice-cold methanol is added to a solution of 11-deoxy-17-phenyl-18,19,20-trinor-PGE$_2$ (Preparation 15, 650 mg.) in 30 ml. of methanol at −5° C. The mixture is stirred for an additional 5 min., made slightly acidic by addition of acetic acid, and concentrated under reduced pressure. The residue is extracted with ethyl acetate and the organic phase is washed with water, dilute aqueous sodium bicarbonate and brine. The residue is thereafter dried over sodium sulfate and concentrated under reduced pressure. This concentrate is chromatographed over silica gel, wet packed in ethyl acetate, eluting with 2, 4, 7.5 and 10 percent ethanol in ethyl acetate. Those fractions containing the 9β-hydroxy title compound free of starting material and impurities as shown by thin layer chromatography are combined to yield the title compound.

Likewise those fractions containing the 9α-hydroxy epimer are combined, preparing the corresponding PGF$_{2\alpha}$ -type compound.

Following the procedure of Example 4, but using those PGE$_2$-type compounds described following Preparation 15, there are prepared the corresponding PGF$_{2\beta}$ -type compounds.

Further, following the procedure of Example 4, but using in place of the PGE$_2$-type compound the PGE$_1$-type compounds described in Preparation 16 and the paragraphs following Preparation 16, there are obtained the corresponding 11-deoxy-18,19,20-trinor-PGF$_{1\beta}$ -type compounds and 11-deoxy-18,19,20-trinor-PGF$_{1\alpha}$ -type compounds of this invention.

Further, following the procedure of Example 4, but using the 13,14-dihydro-PGE$_1$-type compounds of Example 3 and the paragraph following Example 3, there are obtained the corresponding 13,14-dihydro-PGF$_{1\alpha}$ and 13,-14-dihydro-PGF$_{1\beta}$ -type compounds of this invention.

EXAMPLE 5

5α-Hydroxy-2β(3β-hydroxy-5-phenyl-pentyl)-1α-cyclopentaneacetic acid, γ-lactol, tetrahydropyranyl ether (Formula X: Y is —CH$_2$CH$_2$—, M$_6$ is

L$_1$ is

and R$_7$ is

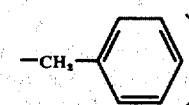

and its 3β-epimer.

5α-Hydroxy-2β-[(3S)-3-hydroxy-5-pehnyl-trans-1-pentenyl]-1α-cyclopentaneacetic acid, γ-lactone (4.5 g., as prepared in Preparation 11), 900 mg. of 5 percent palladium-on-charcoal catalyst, and 450 ml. of ethyl acetate are stirred at ambient temperature under one atmosphere of nitrogen for one hr. When hydrogen uptake ceases, the reaction mixture is filtered through celite, washed with ethyl acetate, and evaporated to yield 5α-hydroxy-2β[(3S)- 3hydroxy-5-phenylpentyl]-1α-cyclopentaneacetic acid, γ-lactone. This compound is then transformed into the title compound following the procedure described in Example 11 for transformation of the lactone therein into the lactol tetrahydropyranyl ether.

Following the procedure described above, but using the 3β-hydroxy lactone, the corresponding 3β-hydroxy lactol, tetrahydropuranyl ether is prepared. Following the procedure of Example 5, but using in place of the 3-hydroxy lactone starting material described therein the 3-methoxy lactones of Preparation 12 there is prepared the correspondng 3α-hydroxy 2β-(3-methoxy-5-phenylpentyl) -1α-cyclopentaneacetic acid, γ-lactol, tetrahydropyranyl ethers.

Following the procedure of Example 5, there are obtained the 3-hydroxy or 3-methoxy, 4-methyl or 4,4-dimethyl lactol ether products with optional substitution on the 5-phenyl, by using the lactone starting material described in Examples 11 and 12. Likewise there are obtained the 3-hydroxy or 3-methoxy substituted phenyl lactol tetrahydropyranyl ethers.

EXAMPLE 6

5α-Hydroxy-2β-(3α-hydroxy-3-methyl-5-phenylpentyl) 1α-cyclopentaneacetic acid, γ-lactol, tetrahydropyranyl ether Formula X: Y is —CH$_2$CH$_2$—, M$_6$ is

L$_1$ is

and R$_7$ is

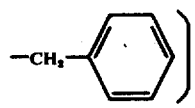

and is 3β-epimer. Refer to Chart D.

A. To a stirred solution of 26.5 g of 5α-hydroxy-2β-[(3RS)-3-hydroxy-3-methyl-5-phenyl-trans-1-pentenyl] 1α -cyclopentaneactic acid γ-lactone (prepared according to Preparation 13 ) in one 1 of dry pyridine under a nitrogen atmosphere and cooled in an ice-bath is added 500 ml. of benzoyl chloride. The resulting solution is stirred for 15 min. at ambient temperature, and then at 70° C. for 5 hr. Thereafter the solution is cooled to ambient temperature and then to 0° C . in an ice-bath. To this stirred solution is then added 90 ml of water in dropwise fashion. This resulting mixture is then stirred at 0° C. for an additional 30 min. then at ambient temperature for 24 hr. The resulting mixture is then equilibrated with a mixture of one 1. ethyl acetate and 4 1. aqueous sulfuric acid. The phases are separated and the aqueous phase is extracted 4 times with ethyl acetate. The organic extracts are combined, washed with water, and then aqueous sodium bicarbonate wash is backwashed with ethyl acetate. The organic extracts are then combined washed with brine and dried using sodium sulfate. Upon evaporation the crude product is obtained. Silica gel chromatography eluting with 50 percent ethyl acetate in Skellysolve B yields a 3(RS)-benzoyloxy compound.

B. A column is packed with 1800 g. of silica gel slurried in methylene chloride. 24.2 g. of the benzoate of part A above is dissolved in several ml. of methylene chloride and applied to the column. Elution with 2 percent acetone in methylene chloride yields the less polar 15(S) and more polar 15(R) epimers.

C. Following the procedure of Preparation 13 each of the lactones of part B is transformed into the title compound.

Following the procedure of Example 14 and 15, but using in place of the lactone starting materials therein the 3-methyl or 3-methoxy and/or 4-methyl or 4,4-dimethyl and/or 17-phenyl or 17-substituted phenyl lactones described according to Examples 11, 12, and 13 there are prepared the corresponding saturated lactols.

EXAMPLE 7

11-Deoxy-17-phenyl-18,19,20-trinor-13,14-dihydro PGF$_{2\alpha}$ , PGF$_{2\beta}$ , and PGE$_2$ (Formula XII, XIV, or XVI: g is 3, R$_1$ is hydrogen, Y is —CH$_2$CH$_2$—, M$_1$ is

L$_1$ is

and R$_7$ is respectively

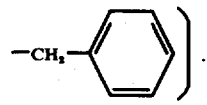

Following the procedure of Example 1, Preparation 15, and Example 4, but using in place of the lactol starting material of Example 1, the Example 5 saturated lactol starting material there are respectively prepared the title compounds.

Following the procedure described in Example 7 there are prepared the corresponding 15-methyl or 15-methyl ether and/or 16-methyl or 16,16-dimethyl and 17-phenyl or 17-substituted phenyl 13,14-dihydro-PG$_2$-type compounds of this invention by using in place of the lactol staring material of Example 7 the various lactols described following Example 6.

EXAMPLE 8

2a,2b-Dihomo-11-deoxy-17-phenyl-18,19,20-trinor-PGF$_{2\alpha}$ (Formula XII: wherein g is 5, R$_1$ is hydrogen, Y is trans-CH=CH—, M$_1$ is

L$_1$ is

and R$_7$ is

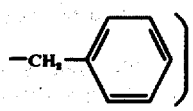

Following the procedure of Example 1, but using in place of (4-carboxybutyl)triphenyl phosphonium bromide the compound of Preparation 14, (6-carboxyhexyl)triphenylphosphonium bromide, the title compound is prepared.

Following the above procedures, but using in place of (4-carboxybutyl)triphenylphosphonium bromide therein (6-carboxyhexyl)triphenylphosphonium bromide, there are prepared the corresponding 2a, 2b-dihomo-11-deoxy-PG-type compounds of this invention.

EXAMPLE 9

11-deoxy-17-phenyl-18,19,20-trinor-PGF$_2$, Adamantanamine Salt (Formula XIV: wherein R$_1$ is admantanamine, Y is trans-CH=CH—, M$_1$ is

L$_1$ is

and R$_7$ is

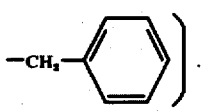

A mixture of 11-deoxy-17-pheny-18,19,20-trinor-PGF$_2$ (Example 1, 0.34 g.) and adamamntanamine (0.27 g) in 33 ml. of diethyl ether is diluted with hexane then concentrated to 10 ml. This mixture is chilled at −10° C. overnight yielding crude product. The title compound is obtained therefrom by purificaton.

We claim:
1. A compound of the formula

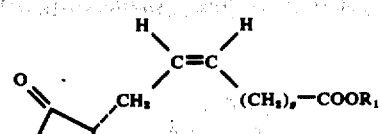

or a mixture comprising that compound and the enantiomer thereof;

wherein g is 3 to 5, inclusive;
wherein R$_1$ is hydrogen, alkyl of one to 12 carbon atoms, inclusive cycloalkyl of 3 to 10 carbon atoms, inclusive, aralkyl of 7 to 12 carbon atoms, inclusive, phenyl, phenyl substituted with one or two alkyl of one to 3 carbon atoms, inclusive, or chloro, or a pharmacologically acceptable cation;
wherein L$_1$ is

or a mixture of

and

wherein R$_3$ and R$_4$ are hydrogen or methyl, being the same or different;
wherein M$_1$ is

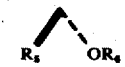

or

wherein R$_5$ and R$_6$ are hydrogen or methyl, with the proviso that R$_5$ is methyl only when R$_6$ is hydrogen and R$_6$ is methyl only when R$_5$ is hydrogen;
wherein R$_{21}$, R$_{22}$, R$_{23}$, R$_{24}$, and R$_{25}$, are hydrogen, fluoro, chloro, trifluoromethyl, alkyl of one to 4 carbon atoms, inclusive, or —OR$_8$ wherein R$_8$ is alkyl of one to 3 carbon atoms, inclusive, with the proviso that at least two of R$_{21}$, R$_{22}$, R$_{23}$, R$_{24}$, and R$_{25}$ are hydrogen, and not more than two of R$_{21}$, R$_{22}$, R$_{23}$, R$_{24}$, and R$_{25}$ chloro, fluoro, trifluoromethyl or —OR$_8$, with the further proviso that R$_{21}$, R$_{22}$, R$_{23}$, R$_{24}$, and R$_{25}$ are all hydrogen only when at least one of R$_3$, R$_4$, R$_5$, and R$_6$ is methyl.

2. A compound according to claim 1, wherein $M_1$ is

3. A compound according to claim 2, wherein g is 5.

4. A compound according to claim 3, wherein $R_{21}$, $R_{22}$, $R_{23}$, $R_{24}$, and $R_{25}$ are hydrogen, or four of $R_{21}$, $R_{22}$, $R_{23}$, $R_{24}$, and $R_{25}$ are hydrogen and one of $R_{21}$, $R_{22}$, $R_{23}$, $R_{24}$, and $R_{25}$ is chloro fluoro, or trifluoromethyl.

5. A compound according to claim 4, wherein $M_1$ is

6. A compound according to claim 5, wherein $L_1$ is

7. A compound according to claim 6, wherein $R_1$ is hydrogen, alkyl of one of 4 carbon atoms, inclusive, or a pharmacologically acceptable cation.

8. 2a,2b-Dihomo-11-deoxy-17-(m-chlorophenyl)-18,19,20-trinor-$PGE_2$, methyl ester, a compound according to claim 7

9. 2a,2b-Dihomo-11-deoxy-17-(p-fluropheny)-18,19,20-trinon-$PGE_2$, methyl ester, a compound according to claim 7.

10. 2a,2b-Dihomo-11-deoxy-17-(m-trifluoromethylphenyl)- 18,19,20-trinor-$PGE_2$, methyl ester a compound according to claim 7.

11. A compound according to claim 1 wherein g is 3.

12. A compound according to claim 11, wherein $R_{21}$, $R_{22}$, $R_{23}$, $R_{24}$, and $R_{25}$ are hydrogen or four of $R_{21}$, $R_{22}$, $R_{23}$, $R_{24}$, and $R_{25}$ are hydrogen and one of $R_{21}$, $R_{22}$, $R_{23}$, $R_{24}$, and $R_{25}$ is chloro, fluoro, or trifluoromethyl.

13. A compound according to claim 12, wherein $R_5$ is methyl.

14. A compound according to claim 12, wherein $R_6$ is methyl.

15. A compound according to claim 12, wherein $R_5$ and $R_6$ are hydrogen.

16. A compound according to claim 15, wherein $R_3$ is methyl and $R_4$ is hydrogen.

17. A compound according to claim 15, where $R_3$ and $R_4$ are both methyl.

18. A compound according to claim 15, wherein $R_3$ and $R_4$ are hydrogen.

19. 11-Deoxy-17-(M-chlorophenyl)-18,19,20-trinor-$PGE_2$, a compound according to claim 18.

20. 11-Deoxy-17-(P-fluorophenyl)-18,19,20-trinor-$PGE_2$, a compound according to claim 18.

21. 11-Deoxy-17-(m-trifluoromethylphenyl)-18,19,20trinor-$PGE_2$, a compound according to claim 18.

22. A compound according to claim 1, wherein $M_1$ is

* * * * *